United States Patent
Schönbrunn et al.

(10) Patent No.: US 9,523,076 B2
(45) Date of Patent: Dec. 20, 2016

(54) METHOD FOR THE IDENTIFICATION AND SEPARATION OF NON-REGULATORY T-CELLS FROM A MIXTURE OF REGULATORY T-CELLS

(75) Inventors: Anne Schönbrunn, Berlin (DE); Dan Robin Miller, Berlin (DE); Siegfried Kohler, Berlin (DE); Marco Frentsch, Berlin (DE); Andreas Thiel, Berlin (DE)

(73) Assignee: MILTENYI BIOTEC GMBH, Bergisch Gladbach (DE)

( * ) Notice: Subject to any disclaimer, the term of this patent is extended or adjusted under 35 U.S.C. 154(b) by 1094 days.

(21) Appl. No.: 12/878,871

(22) Filed: Sep. 9, 2010

(65) Prior Publication Data

US 2011/0097313 A1    Apr. 28, 2011

(30) Foreign Application Priority Data

Sep. 10, 2009    (DE) .................. 10 2009 040 716

(51) Int. Cl.
| | | |
|---|---|---|
| *G01N 33/569* | (2006.01) | |
| *A61K 35/12* | (2015.01) | |
| *C12N 5/0783* | (2010.01) | |

(52) U.S. Cl.
CPC ....... *C12N 5/0636* (2013.01); *G01N 33/56972* (2013.01); *A61K 2035/122* (2013.01); *G01N 2333/70575* (2013.01)

(58) Field of Classification Search
CPC ............... A61K 2035/122; G01N 2333/70575; C12N 5/0636
(Continued)

(56) References Cited

U.S. PATENT DOCUMENTS

2003/0147865 A1* 8/2003 Salomon ............... A61K 35/17
                                                       424/93.21
2004/0147021 A1* 7/2004 Schuler et al. ............... 435/372
(Continued)

FOREIGN PATENT DOCUMENTS

DE    102009040716 B4    7/2011
EP         1420253 A1    5/2004
(Continued)

OTHER PUBLICATIONS

BD Pharmingen™. Technical Data Sheet: PE conjugated mouse anti-human CD137 (4-1BB). May 7, 2005. Available at URL: http://www.bdbiosciences.com/external_files/pm/doc/tds/human/live/web_enabled/36005X_555956.pdf.
(Continued)

*Primary Examiner* — Sharmila G. Landau
*Assistant Examiner* — Sheridan MaCauley
(74) *Attorney, Agent, or Firm* — Kilpatrick Townsend and Stockton LLP

(57) ABSTRACT

The present invention relates to a method of identifying and separating non-regulatory T-cells (conventional T-cells) from a mixture comprising regulatory T-cells by using of the CD154 molecule (CD40 ligand) through depletion of CD154+ T-cells from the mixture or in combination with additional positive selection of Treg using markers that are specific for regulatory T-cells, such as for example, CD25, GITR, CTLA4 or markers which are specific for activated regulatory T-cells, such as, for example, CD137, "latent TGF-beta (LAP)", GARP (LRRC32), CD121a/b, thereby generating a cell composition of activated Treg cells. The invention relates also to a kit comprising an antibody for detecting CD154 and at least one additional antibody for detecting markers for activated or non-activated regulatory
(Continued)

T-cells. The antibodies can be coupled to a fluorescent dye or magnetic microparticles.

18 Claims, 12 Drawing Sheets

(58) Field of Classification Search
USPC .......................................................... 424/94.5
See application file for complete search history.

(56) References Cited

U.S. PATENT DOCUMENTS

| 2005/0107585 | A1* | 5/2005 | Murray et al. ................ | 530/350 |
| 2006/0121027 | A1* | 6/2006 | Frentsch et al. ........... | 424/140.1 |
| 2006/0193856 | A1 | 8/2006 | Taylor et al. | |

FOREIGN PATENT DOCUMENTS

| EP | 1840569 A1 | 10/2007 | | |
| WO | 2005-124346 A1 | 12/2005 | | |
| WO | 2007/110249 A1 | 10/2007 | | |
| WO | WO 2009036521 A1 * | 3/2009 | ............. | G01N 33/50 |

OTHER PUBLICATIONS

Choi et al. 4-1BB-dependent inhibition of immunosuppression by activated CD4+CD25+ T cells. Journal of Leukocyte Biology, May 2004, p. 785-791, vol. 75.

Frentsch et al. Direct access to CD4+ T cells specific for defined antigens according to CD154 expression. Nature Medicine, 2005, p. 1118-1124, vol. 11.

Jarvinen et al. CD154 on the surface of CD4+CD25+ regulatory T cells contributes to skin transplant tolerance. Transplantation, Nov. 15, 2003, p. 1375-1379, vol. 76, No. 9.

Miltenyi Biotec, Inc. Miltenyi Biotech Data Sheet. CD154 MicroBead Kit. Human. Order No. 130-092-658, 2010, 4 pages.

Nishikawa et al., Induction of Regulatory T cell-resistant helper CD4+ T cells by bacterial vector. Blood, Feb. 2008, p. 1404-1412, vol. 111, No. 3.

Kleinewietfeld et al. CD49d provides access to "untouched" human Foxp3+ Treg free od contaminating effector cells. Blood, Jan. 2009, p. 827-836, vol. 113.

Li Hua-Ping et al. Fusion of hC3d3 to hCGβ enhances responsiveness in vitro of human peripheral immunocompetent cells upon the antigen primary challenge. Journal of reproductive immunology, Jul. 2008, p. 115-124, vol. 78, No. 2.

Putnam Amy L et al. Expansion of Human Regulatory T-Cells From Patients With Type 1 Diabetes. Diabetes, Mar. 2009, pp. 652-662, vol. 58.

Rausch et al. Functional Analysis of Effector and Regulatory T Cells in a Parasitic Nematode Infection. Infection and Immunity, 2008, p. 1908-1919, vol. 76, No. 5.

Tran Dat Q et al. Selective expression of latency-associated peptide (LAP) and IL-1 receptor type I/II (CD121a/CD121b) on activated human FOXP3+ regulatory T cells allows for thier purification from expansion cultures. Blood, May 2009, p. 5125-5133, vol. 113, No. 21.

Tran Dat Q et al. GARP (LRRC32) is essential for the surface expression of latent TGF-beta on platelets and activated FOXP3+ regulatory T cells. PNAS, Aug. 2009, p. 13445-13450, vol. 106, No. 32.

BD Biosciences, "Human Regulatory T Cell Analysis, A new approach using CD127, CD25, and CD4", accessed via web-address; www.bdbeurope.com/images/bdb/dm/06076IF1_1166.pdf on May 13, 2015, 12 pages.

Miltenyi Biotec, "CD154 Detection Cocktails, mouse", accessed via web-address; www.miltenyuibiotec.com/download/datasheets_en/1000/MiltenyiBiotec_DataSheet_CD154-Detection-Cocktail-(PE),-mouse_130-0-93-084.pdf on May 13, 2015, 3 pages.

Nishikawa, H. et al., "Induction of regulatory T cell-resistant helper CD4+ T cells by bacterial vector", Blood (2008) 111 (3) 1404-12.

Rausch, S. et al., "Functional analysis of effector and regulatory T cells in a parasitic nematode infection", Infection and Immunity, (2008) 76 (5) 1908-19.

Ianni et al., "Tregs prevent GVHD and promote immune reconstitution in HLA-haploidentical transplantation," Blood, vol. 17, No. 14, Apr. 7, 2011, pp. 3921-3928.

Martelli et al., "HLA-haploidentical transplantation with regulatory and conventional T-cell adoptive immunotherapy prevents acute leukemia relapse," Blood, vol. 124, No. 4, Jul. 24, 2014, pp. 638-644.

Noyan et al., "Isolation of human antigen-specific regulatory T cells with high suppressive function," Eur. J. Immunol., vol. 33, 2014, pp. 2592-2602.

Pierini et al., "NK Cell and CD4+FoxP3+ Regulatory T Cell Based Therapies for Hematopoietic Stem Cell Engraftment," Stem Cells International, vol. 2016, Article ID 9025835, 11 pages, retrieved at http://dx.doi.org/10.1155/2016/9025835.

Safinia et al., Regulatory T cells: serious contenders in the promise for immunological tolerance in transplantation, Frontiers in Immunology, vol. 6, Article 438, Aug. 2015, pp. 1-16.

Theil et al., "Adoptive transfer of allogeneic regulatory T cells into patients with chronic graftversus-host disease," Cytotherapy, International Society for Cellular Therapy; Published by Elsevier Inc. on Jan. 6, 2015; http://dx.doi.org/10.1016/j.jcyt.2014.11.005, 14 pages.

* cited by examiner

METHOD FOR THE IDENTIFICATION AND SEPARATION OF NON-REGULATORY T-CELLS FROM A MIXTURE OF REGULATORY T-CELLS

RELATED APPLICATIONS

This application claims Paris Convention priority under 35 USC §119 to DE10-2009-040716.2 filed Sep. 10, 2009, the complete disclosure of which is hereby incorporated by reference.

FIELD OF THE INVENTION

The invention pertains in general to the field of immunology, in particular to the field of cell separation. The present invention refers to the use of the CD154 molecule (CD40 ligand) for identifying and separating non-regulatory T-cells (conventional T-cells) from a mixture comprising regulatory T-cells.

BACKGROUND

Specific T-cells, which actively suppress unwanted immune responses such as, for example, to endogenous structures (auto-antigens) exist in the organism. They are referred to as regulatory T-cells (Treg). Regulatory T-cells are essentially involved in the life-long maintenance of peripheral tolerance to auto-antigens. They are produced in the thymus, but the activity thereof is greatly reduced with increasing age.

Regulatory T-cells may lead to suppression of anti-tumor responses (Onizuka et al., Cancer Res. 59: 3128-3133 (1999); Shimizu et al., J. Immunol. 163:5211-5218 (1999) both incorporated by reference for all purposes), because many tumor antigens represent classical auto-antigens. By contrast, reduced numbers of Treg or functional alterations in Treg may lead to autoimmune diseases during which endogenous structures are attacked in an uncontrolled manner like foreign substances or pathogens.

Treg are involved in maintenance of immunological self-tolerance, in that they inhibit the activation of auto-reactive T-cells. They are capable of suppressing both cytokine production as well as the proliferation of such potentially pathogenic T-cells. An essential step in the identification of regulatory T-helper cells was the characterization of CD4+ T-helper cells, which include the constitutive alpha-chain protein of the interleukin-2 (IL-2) receptor (CD25) as a surface membrane protein.

The functional significance and the exact molecular mechanisms of the suppression of these CD25+CD4+ regulatory T-cells and also the manner in which they arise have until now not been elucidated. Since the CD25 receptor is also expressed by subpopulations of non-regulatory T-cells, this marker can only be used provisionally for analyzing and concentrating Treg. CD25 cannot, however, be used particularly for identifying and separating activated antigen specific regulatory T-cells.

Isolation of Treg without contaminating conventional T-cells and in particular of Treg specific for certain antigens is, nevertheless, one of the great therapeutic aims. This is also true for the analysis of Treg and antigen-specific Treg. (Auto)antigen-specific Treg are a specific means for suppressing unwanted immune responses such as, for example, autoimmune reactions in rheumatoid arthritis (RA), multiple sclerosis (MS), atherosclerosis (AS), diabetes, and psoriasis. Other unwanted immune responses in which Treg would represent a specific means are GvHD (graft versus host disease) in allogeneic stem cell transplantations or transplant rejection in organ transplantations (Hara et al., J. Immunol. 166: 3789-3796 (2001); Taylor et al., J. Exp. Med. 193: 1311-1318 (2001), both incorporated by reference for all purposes). Allergies also represent unwanted immune responses for which only a few therapeutic options have been available to date. A therapeutic treatment with Treg, which is based on the natural principal of peripheral tolerance and has been demonstrated in many experimental models would involve no side effects by comparison with conventional immunosuppressive medicaments and would be curative.

In relation to the stated importance of Treg, the molecules and mechanisms involved in the suppression, and reliable Treg markers, are of great importance. A molecular biological Treg marker, the transcription repressor FoxP3, which belongs to the Forkhead-family, is acknowledged in the art (Hori et al (2003) Science 99(5609): 1057-61, incorporated by reference for all purposes). In addition, regulatory T-cells can be identified on the bases of expression of the CD25 molecule (Thornton and Shevach (1998) J. Exp. Med. 188 287-296; Sakaguchi et al. (1995) J. Immunol. 155 1151-1164, both incorporated by reference for all purposes).

To date, however, it has not been possible to identify and isolate those Treg cells, which recognize a specific antigen. This would be possible if specifically activated Treg could be separated. This would be a prerequisite for specific therapies with Treg, for example, for autoimmune diseases in which the autoimmune reactions underlying the disease should be suppressed, but not those immune reactions launched against tumor cells.

According to Choi et al. (2004, J. Leukocyte Biology 76:1-7, incorporated by reference for all purposes), no evidence exists that CD137 (4-1BB) can be employed as a discriminative marker for Treg versus CD25. In an international application (WO 2007/110249, incorporated by reference for all purposes), it is described that Treg selectively express CD137 at about 4 hours after activation, whereas conventional T-cells only start to express CD137 after about 12 to 16 hours. Although this early time window can be used to isolate regulatory T-cells only a few hours after activation, this method is prone to errors and therefore is of little practical use. A strong variability in the activation state of the T-cells after obtaining them from blood or tissues as well as the variability of the special kinetics of CD137 on the individual T-cells leads to a contamination of the regulatory T-cells with conventional T-cells, which can be small or large, depending on the time point of the isolation, and which limits the usability of isolated cells dramatically. By using an early time point for separating the cells, the contamination can be kept small, although the yield of the isolated regulatory T-cells is grossly decreased, since not all regulatory T-cells have yet become positive for CD137. As the number of regulatory T-cells, in particular of antigen-specific regulatory T-cells is small to begin with, the decrease in yield diminishes the usability of the method, since many therapeutic uses can no longer be applied.

Therefore, to date, it is not possible to identify and separate the contaminating effector cells (e.g. FoxP3 negative and/or cytokine positive) from the regulatory T-cells (defined by the expression of known markers, in particular CD25, CD25+CD127−, GITR+) or to differentiate antigen-activated regulatory T-cells from activated conventional T-cells.

The term "conventional T cells" as used herein refers to all T cells which do not belong to the "naturally occurring"

regulatory T cells which are characterized by stable expression of the transcription factor Foxp3+ and which typically express CD25 constitutively and no or low levels of CD127. Conventional T cells especially refer to T cells which exert immune activating effector functions, i.e. production of effector cytokines such as IL-2, IFN-gamma, IL-4, IL-5, IL-9, IL-17, IL-22.

It is thus difficult, based on the present state of the art, to identify and/or isolate regulatory T-cells. Markers described thus far do not allow the possibility of identifying the totality of regulatory T-cells, because not all regulatory T-cells expressed defined specific markers. Accordingly, it is only possible to identify and/or separate subpopulations, such as, for example only the Treg, which strongly expresses the CD25 receptor. Furthermore, various other cell subpopulations that have the same cell surface markers (such as CD4 for Th1 and Th2, or other Th-cells or CD25 for activated T-cells or B-cells) cannot be distinguished from regulatory T-cells.

In particular, it is not possible to identify activated Treg after stimulation with defined antigens by means of specific activation markers. Although activation of regulatory Th-cells leads to enhanced expression of CD25 and CD38, they are expressed like all other described T-cell activation markers also in other T-cells, so that it has not been possible to separate any antigen-specific Treg by means of specific activation markers.

Frentsch et al. (2005, Nat Med. 11(10):1118-24) and the application EP 1 420 253, both incorporated by reference for all purposes, disclose that CD154 (CD40 ligand) is expressed on all activated T-cells, wherein no distinction is made by the authors between conventional and regulatory T-cells regarding expression of CD154. Therefore, it is not known whether CD154 can be used to discriminate between activated conventional and activated regulatory T-cells.

Rausch et al (2008, Infection and Immunity, 76(5):1908-1919, incorporated by reference for all purposes) disclose that they were able to identify murine antigen-specific Teff and Treg cells by the expression of CD154. The authors in fact assumed that CD154 is also expressed by antigen-activated Treg and could be used for positive selection of antigen-activated Treg.

Therefore, these murine data do not suggest using CD154 as discriminative marker between activated conventional and activated regulatory T-cells.

Most of the methods used to identify and/or isolate regulatory Th-cells on the basis of the expression of a particular cell surface marker depend on recognition of a marker and binding of an antibody. When it is not possible to use a single marker to identify and/or isolate a particular cell type, it is necessary to find a combination of markers and the cognate antibodies (Levings et al., J Exp. Med. 193 (11): 1295-1302 (2001), incorporated by reference for all purposes). Such experiments may in practice be very complicated and difficult to carry out. Moreover, it is possible that the binding of the antibodies influences the activity of the target cell or the expression of other markers, thus having a negative influence on the identification and/or separation process with the other antibodies.

To date, no specific identification and/or separation of exclusively living regulatory T-cells has been carried out. The only specific marker described to date, FoxP3, may moreover, according to recent investigations, be induced also in non-regulatory T-cells (Fontenot J. D. 2003; Hori S. et al. 2003, both incorporated by reference for all purposes). Since FoxP3 is present as an intracellular protein, it is further not possible according to the present state of the art to identify and/or isolate living regulatory cells, for example, on the basis of a FoxP3 antibody. Again, the problem that arises is that only the totality of the Treg can be identified, but not Treg specific for pre-defined antigens. A reliable identification and/or separation of the Treg and in particular of antigen-specific Treg have therefore not been possible.

BD Pharmingen™: "Technical Data Sheet: PE conjugated mouse anti-human CD137 (4-1BB)", May 7, 2005 (available on the world-wide-web at bdbiosciences.com/external_files/pm/doc/tds/hu-man/live/web_enabled/36005X_555956.pdf, also discloses that the CD137 marker represents an activation marker for all T-cells. The application WO 2005/124346, incorporated by reference for all purposes, also merely describes CD137 as being a marker on CD4$^+$ CD25$^+$; however, the publication does not disclose that CD4$^+$CD25$^+$ especially express at a particular time during activation of the CD137 marker as compared to CD4$^+$ CD25$^-$ T-cells. The authors of WO 2005/124346 disclose, on the other hand, that both cell populations of CD4$^+$ CD25$^+$ and CD4$^+$ CD25$^-$ T-cells express the CD137 marker to the same extent after activation thereof. The documents mentioned represent the opinion in the art that the CD137 marker cannot be used as a discriminatory marker for CD25$^+$ Treg-cells versus CD25$^-$ T-cells. In particular, BD Pharmingen™ describes a PE-conjugated mouse anti-human CD137 antibody. WO 2005/124346 discloses the co-stimulation of freshly isolated CD4$^+$ CD25$^+$ mouse Treg-cells via CD137. The Treg-cells are not stimulated via CD137, but through the presence of strong acting stimuli such as CD3. On the basis of the disclosure mentioned, a skilled artisan assumes that most of the so-called fresh Treg-cells do not express CD137. For example, it is shown in FIG. 5 of WO 2005/124346 that co-stimulation with 4-1BBL exerts activating properties in particular also on CD25$^-$ cells. It is disclosed in FIG. 1$d$ in an unambiguous fashion that CD4$^+$ CD25$^+$ and CD4$^+$ CD25$^-$ T-cells both express CD137 during activation, so that the publications mentioned do not motivate the skilled artisan to use CD137 for specific presentation or isolation of CD4$^+$ CD25$^+$ Treg-cells from cell mixtures.

In WO 2007/110249, incorporated by reference for all purposes, it is disclosed that Treg express CD137 selectively within an early time frame after activation (only after about 4 hours), whereas conventional T-cells begin to express CD137 after about 12 to 16 hours. Although this time frame may be used for identifying activated regulatory T-cells, the variability of the expression kinetics as well as the short stimulation time leads to a massive decrease of cell purity and yield. There is no method available for enrichment of activated Treg cells allowing the simultaneous depletion of activated conventional T cells and Foxp3+ T cells with instable Foxp3 expression.

SUMMARY OF THE INVENTION

The present invention relates to a method of identifying and separating non-regulatory T-cells (conventional T-cells) from a mixture comprising regulatory T-cells by using of the CD154 molecule (CD40 ligand) through depletion of CD154+ T-cells from the mixture or in combination with additional positive selection of Treg using markers that are specific for regulatory T-cells, such as for example, CD25, GITR, CTLA4 or markers which are specific for activated regulatory T-cells, such as, for example, CD137, "latent TGF-beta (LAP)", GARP (LRRC32), CD121a/b. The invention relates also to a kit comprising an antibody for detecting CD154 and at least one additional antibody for detecting markers for activated or non-activated regulatory T-cells.

The antibodies can be coupled to a fluorescent dye or magnetic microparticles. The regulatory T-cells and the conventional T-cells can be activated with either polyclonal or specific antigens. The activation can be performed in vitro or in vivo and can be performed on un-separated T-cells or pre-selected regulatory T-cells, for example, using CD25, CTLA-4 (CD152), GITR or other typical markers for regulatory T-cells.

DETAILED DESCRIPTION OF THE INVENTION

Figure 1:
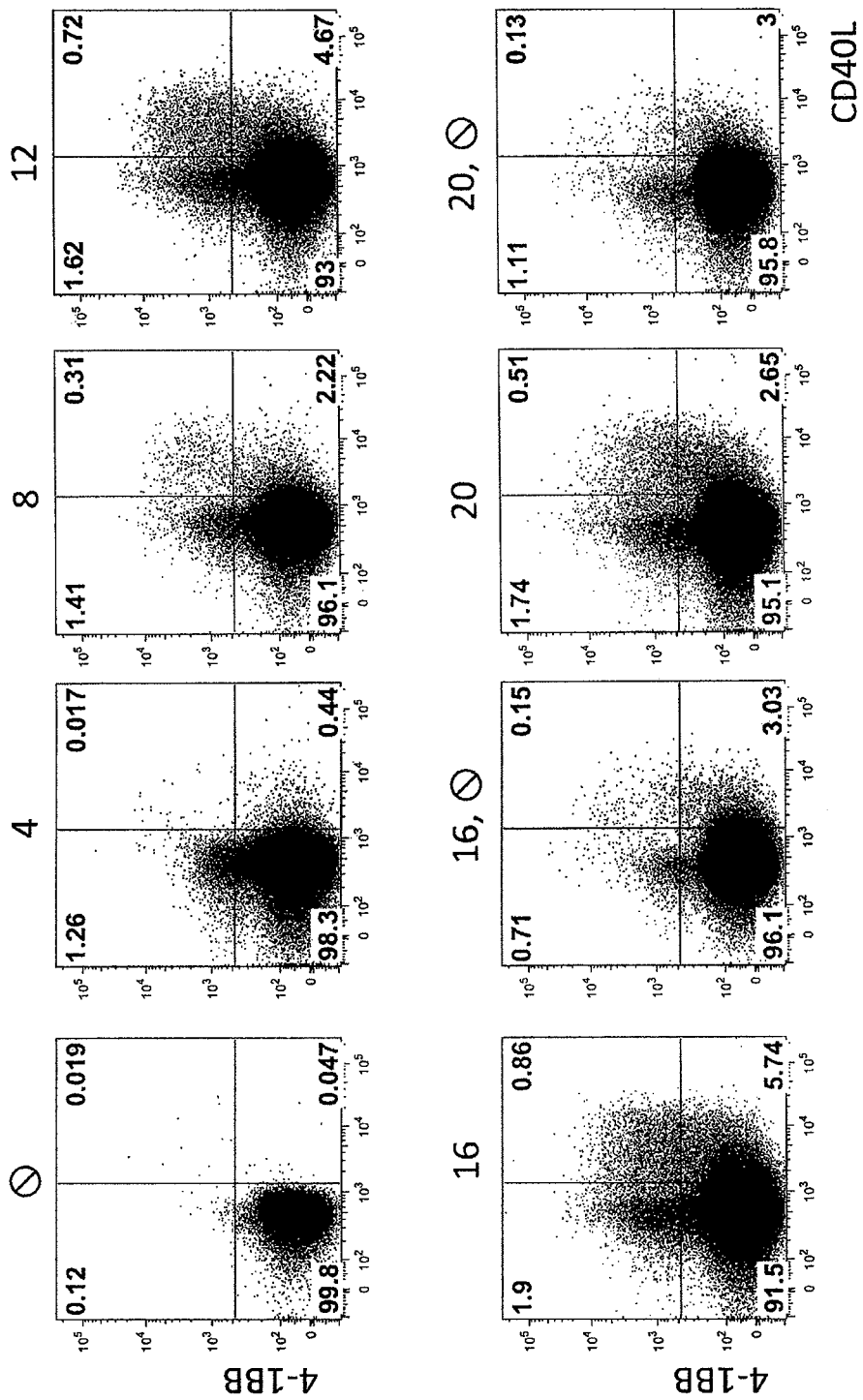
FIG. 1 shows that shortly after stimulation a large fraction of the CD137+ Treg also expressed CD154.

A method was surprisingly found for removing living, activated conventional T-cells from mixtures comprising regulatory T-cells, wherein CD154 can be used as a marker and wherein CD154-specific antibodies can be used to identify and/or remove activated conventional T-cells. By combining the depletion of conventional T-cells with a separation step (preceding or consecutive) in which regulatory T-cells are identified and enriched (either using conventional markers for non-activated regulatory T-cells, like CD25, CTLA4 or GITR, or through labeling them with a marker specific for activated Treg like CD137, latent TGF-beta (LAP), GARP (LRRC32), CD121a/b), the purity and yield of the activated regulatory T-cells can be largely increased, which is a prerequisite for many therapeutic and diagnostic applications.

As used herein, the terms "depletion", "depleting" and the like, in the context of cell isolation, purification or enrichment, have the normal meaning in the art, and refer to removal of specified cells (e.g., CD154+ cells) from a mixture or starting population of cells. Method for depletion are well known in the art and are described herein, and include, for example, FACS or MACs sorting in which specified cells in a population (e.g., CD154+ cells) are labeled and removed from the population of cells resulting in a new population in which the specified cells are absent or present in a lower proportion than in the starting population. It will be recognized that "depletion" does not require that the specified cells be entirely removed or that the new population be entirely free of the specified cells. Typically, depleting specified cells from a population means reducing the representation of such cells (measured as a percentage of all of the cells in the population) by at least about 50%, at least about 60%, at least about 70%, at least about 80%, at least about 90%, at least about 95%, at least about 98%, or at least about 99%).

As used herein, the term "positive selection", in the context of cell isolation, purification or enrichment, has the normal meaning in the art, and refers to the enrichment of specified cells (e.g., CD137+ cells) from a mixture or starting population of cells. Methods for positive selection are well known in the art and are described herein, and include, for example, FACS or MACS sorting in which specified cells in a population (e.g., CD137+ cells) are labelled and isolated from the population of cells in that the isolated cells result in a new population in which the specified cells are present in a higher proportion than in the starting population.

Therefore, the invention refers to the teaching that activated, and in particular, antigen specifically activated conventional T-cells can be separated from $CD4^+$ $CD25^+$ Treg that also have been activated by using the marker CD154 through depletion of the CD154+ cells from the mixture, since activated Treg express no CD154.

Additionally, regulatory cells can be positively identified and/or separated through the expression of one and/or several markers. For this, all markers known to a person of skill in the art for identifying and/or separating Treg from activated Treg can be used. Preferably, the markers CD137, CD25, CTLA-4 (cytotoxic T lymphocyte antigen-4), GITR (glucocorticoid-induced TNF receptor), FoxP3, IL-10, CD69, ICOS, OX40 and TGFbeta can be used alone or in combination. For this, all markers known to a person of skill in the art for excluding or depleting non-regulatory cells can be used in combination. Particularly preferred is the use of CD137 as a marker for living, activated regulatory cells. Either activated regulatory T-cells are directly identified or separated, or the activation is induced through additional cells, proteins, peptides, pathogens or other substances.

The method can also be used for enrichment of activated regulatory T-cells in a mixture of cells.

In one embodiment of the method is the separating of activated regulatory T-cells from a mixture comprising activated regulatory T-cells and activated conventional T-cells by contacting the cell mixture with a molecule binding CD154 and depletion of CD154+ T-cells from the mixture obtaining a population of activated regulatory T-cells.

Another preferred embodiment of the method is the separating of activated regulatory T-cells from a mixture comprising activated regulatory T-cells and activated conventional T-cells, the method comprising the steps:

a) contacting the cell mixture with
  i. a molecule binding CD154 and depletion of CD154+ T-cells from the mixture; or
  ii. a molecule binding a marker that is specific for regulatory T-cells or that is specific for activated regulatory T-cells and positive selection of the cells that bind to said binding molecule;
b) contacting
  i. the cells of step a) i. with a molecule binding a marker that is specific for regulatory T-cells or that is specific for activated regulatory T-cells and positive selection of the cells that bind to said binding molecule obtaining a population of activated regulatory T-cells; or
  ii. the cells of step a) ii. with a molecule binding CD154 and depletion of CD154+ T-cells obtaining a population of activated regulatory T-cells.

The invention relates to T-cells from mammals, in particular, humans, mice, rats, rabbits or dogs. The DNA and protein sequences of the molecules referred to here are known to a person of skill in the art and are publicly available in databases. When necessary, the sequences can also be obtained using routine laboratory techniques.

The invention also relates to the use of CD154 as well as its homologues and fragments. The homologues may show, for example, a homology of at least 50%, at least 60%, at least 70%, at least 80%, at least 90%, at least 95%, at least 98%, at least 99% to human CD154. The fragments of CD154 are without limitation, i.e. each fragment of naturally occurring CD154 molecule can be used according to the invention. Antibodies, for example, only bind to a part of the CD154 molecule.

The invention refers to both in vitro and in vivo use.

In a further aspect, the invention refers to the surprising teaching that the use of CD154 as a negative selection marker greatly increases the window of time for the use of the marker CD137 for the positive selection of Treg and that 2 to 24 hours after activation, regulatory T-cells can be isolated with great purity and yield.

The separated cells can be collected in a suitable container, for example, a collection tube that allows for the survival and/or growth of the cells. Different media are commercially available and can be used based on the need of the type of cells identified and/or separated. Such media can be, e.g. DMEM, HBSS, DPBS, RPMI, Iscove's medium, X-VIVO™ medium, etc., which may be often supplemented with fetal calf serum, human serum or serum substitutes.

The identified and/or separated cell populations can be used immediately or can be cultivated in vitro after isolation. Subsequently, the cells can be frozen or they can be frozen before being separated. In case the cells are to be stored for a longer period of time it is preferred to do so at around −80° C. or in liquid nitrogen in order to in ensure that the cells can be used again after thawing. For this purpose, the cells are normally stored in DMSO and/or FCS/HS together with a medium, glucose etc. Immediately after the cells have been thawed, the cells can either be used directly for therapeutic purposes or in in vitro experiments or they can be expanded and/or differentiated using growth factors, antigens, cells etc.

It is preferred to identify and isolate the activated regulatory Th-cells from a mixture of cells. The regulatory Th-cells are identified and/or separated from cells samples from mammals, in particular from humans and preferably from patients. The cell samples can be derived, for example, from blood samples containing immune cells (body fluids like peritoneal, cerebral-spinal, pleural liquid, and/or synovial fluid), lavage liquids from hollow organs (airways, lungs), homogenates and aspirates of lymph nodes, spleen, tonsils and/or other lymphatic tissue. The cells can be moved from animal tissues (for example from the spleen or the lymph node of an animal). The cells may also be a part of a blood sample, for example from a subject or a human patient, particularly preferred from a peripheral blood sample.

Activated regulatory Th-cells are directly able to suppress the activity of T-cells. It has been shown in animal models that activated regulatory T-cells can prevent the development of autoimmune diseases, of transplant rejection reactions, and allergic reactions. It is assumed in analogy thereto that activated regulatory T-cells can also suppress the development of chronic immune reactions in humans. By using the CD137 marker, activated regulatory Th-cells are specifically identified and/or separated. Preferably, in vitro activated regulatory Th-cells with the phenotype CD4+ CD25+ FoxP3+ are previously identified and/or separated. The activation occurs preferably using the specific antigens, e.g. peptides, proteins, or pathogens or cells or polyclonal stimuli, e.g. chemical compounds like PMA/ionomycin, superantigens like SEB or PHA or stimulatory antibodies like anti CD3 (or mixtures thereof). In a further embodiment of the invention, living regulatory Th-cells are identified and/or isolated directly ex-vivo.

By using the CD154 marker, activated conventional Th-cells can preferably be removed from mixtures comprising regulatory T-cells, in particular, when additional selection methods using markers for activated/non-activated regulatory cells (CD25, CD137) are used simultaneously or subsequently, which allows for a preferred used of the invention for identifying isolating antigen-specific regulatory Th-cells.

After obtaining a cell mixture from a patient and/or a subject, regulatory T-cells can be enriched using, for example, CD25. These cells can be subsequently stimulated with a particular antigen. For this purpose, antibodies, peptides, proteins, chemicals substances (or mixtures thereof), or pathogens or cells may be used. After a particular activation time, the regulatory Th-cells are identified and/or separated, for example, through the use of the CD137 marker. Thereby, antigen-specific regulatory Th-cells are preferably identified and/or separated.

The cells, which are separated according to the invention, usually stem from an in vivo source and therefore reflect the immunological status of the donor regarding the number, the origin, and the T-cell antigen receptor specificity of the Treg cell. This information may be used in diagnostics referring to immunological disorders, for example, cancer-related immunosuppression, autoimmune disorders, atopical states, etc.

Further, Th-cells of the patient can be contacted in vitro with cells, cell extract separated antigens or proteins of an organ donor before or after the transplantation. Subsequently, the activated regulatory Th-cells are identified and/or separated using the CD137 marker after a suitable activation period.

The cells can be identified and/or separated according to all methods known to the person skilled in the art. Preferred for the identification of cells are in particular cell sorting (e.g. magnetic cell sorting (MACS)), fluorescence activated cell sorting (FACS), ELISA, PCR and/or all fluorescence microscopes known in the art. Particularly preferred is the use of flow-cytometry (FACS). For the separation of the cells, those cell separation systems in which the cells are sorted using a magnetic field (e.g. MACS) or through flow-cytometry (FACS) are particularly preferred. Further, it is preferred the expression of CD137 is measured after stimulation.

The regulatory Th-cells are stimulated by substances known to a person of skill in the art. The expression of CD137 is measured 1 to 18 hours after stimulation. Preferably, the expression is measured 3 to 8 hours after the stimulation.

According to the invention, CD154 is a specific marker for activated conventional T-cells within a time frame of about 0 to 18 hours after activation, preferred within about 0 to 12 hours, particularly preferred within about 0 to 10 hours, especially preferred within about 1 to 8 hours, most referred within about 3 to 8 hours, in particular within 4 hours.

The preferred optimal time point for separation is the time point at which a maximum number of the activated regulatory T-cells express CD137 and at which a minimum number of non-regulatory cells express CD137. This time point can be determined by a skilled artisan through an analysis of the CD137 expression at different time point after stimulation.

In a further preferred embodiment, the regulatory Th-cells are identified and/or separated after a stimulation of the cells in the cell mixture.

In preferred use of the invention, the cells are stimulated by antigens, proteins, peptides, chemical substances, cells, growth factors, antibodies and/or ligands.

The culture may also contain suitable growth factors. Growth factors are defined as molecules that simulate survival, growth, and/or differentiation of a cell either in a culture or within a tissue by interaction with a transmembrane receptor. Growth factors include polypeptides and non-polypeptide factors. Particular growth factors that can be used for culturing the separated and/or used cells include the interleukins, for example, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-22, IL-23, IL-27 etc.; antigens, for example, peptide antigens, protein antigens, like for example alloantigens, preferably together with antigen presenting cells, lectins, for example ConA, [Alpha]-CD3, LPs, etc.

The culture may also contain antibodies or specific ligands (purified ligands, FC fusion proteins or other recombinant forms of the "leucine zipper") for cell surface receptors that may stimulate or inhibit Treg activity. Antibodies or ligands that bind TNFR or other co-stimulating molecules on Treg and stimulate and/or increase Treg activity, that counteract Treg activity (and cause cell division) or that simulate apoptosis of Treg may also be present in the media. Normally, the specific culture parameters serve a particular purpose, for example the maintenance of Treg cell activity, etc.

It is preferred that antibodies for detecting CD154 are used.

As used herein, the term "antibody" is intended to include polyclonal and monoclonal antibodies, chimeric antibodies, haptens and antibody fragments, and molecules which are antibody equivalents in that they specifically bind to an epitope on the product antigen. The term "antibody" includes polyclonal and monoclonal antibodies of any isotype (IgA, IgG, IgE, IgD, IgM), or an antigen-binding portion thereof, including, but not limited to, F(ab) and Fv fragments such as sc Fv, single chain antibodies, chimeric antibodies, humanized antibodies, and a Fab expression library.

One goal is to have a sufficient concentration of antibodies in the reaction mixture such that the efficiency of separation is not limited by too few antibodies. The necessary concentration may be determined through titration.

The method for separating the cells can be any method that maintains the activity of the cells. A preferred method is a phosphate buffered salt solution containing 0.1 to 0.5% BSA or in equal amounts autologous pooled serum or substitute serum substances. Various media are commercially available and may be used depending on the cell type and the experiments that are to be performed. Available media are for example, Dulbecco's modified Eagle's Media (DMEM), Hank's Basic Salt Solution (HBSS), Dulbecco's Phosphate buffered salt solution (DPBS), RPMI, Iscove's Media, X-VIVO™ PBS with 5 mM EDTA etc. often supplemented with fetal calf serum BSA, HSA etc.

The labeled conventional cells are then separated depending on the expression of CD154. The regulatory cells that are not separated can be collected by any method that maintain the vitality of the cells. Normally, the cells are being collected in a collection tube with serum. Various media are commercially available and can be used depending on the identified and/or separated cells, for example, dMEM, HBSS including dPBS, RPMI, Iscove's Media etc., often supplemented with fetal calf serum, autologous or pooled serum or serum substitutes.

It is further preferred that the antigens for detecting CD137 are coupled with a fluorescent dye or to magnetic microparticles.

The antibody is directly or indirectly conjugated to a magnetic reagent, such as a superparamagnetic microparticle (microparticle). Direct conjugation to a magnetic particle is achieved by use of various chemical linking groups, as known in the art.

Alternatively, the antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

For flow-cytometry, e.g. FACS (fluorescence activated cell sorting), and the magnetic cell sorting (e.g. MACS) antibodies are used that may be coupled with fluorescence markers or magnetic microparticles that are known to a person of skill in the art, like FITC, phycoerythrin (PE), allophycocyanin (APC), cascade yellow and peridinin chlorophyll protein (PerCP). The antibodies may also be coupled to haptens and may then be detected with hapten-specific secondary antibodies. A combination of antibodies can be used to detect, analyze and/or isolate various cells with different properties on the basis of markers, like secreted proteins or characteristic surface molecules. In particular, fluorescence labeled antibodies can be used for FoxP3, CD25 and/or CD4 markers. It is particularly preferred to use CD137 antibodies that are coupled to fluorescence dye or to magnetic microparticles. Magnetic microparticles may be used directly or indirectly (hapten for example biotin and anti-hapten microparticle of fluorochrome, e.g. PE or APC and anti-fluorochrome microparticles).

In another preferred embodiment, the regulatory Th-cells are directly identified and/or separated or isolated from blood, peripheral mononuclear blood cells (PBMC), body tissue or cells from tissue fluids.

The regulatory Th cells are normally identified and/or separated from cell samples from mammals (Mamalia), but especially from humans and preferably from test subject and/or patients. The regulatory Th cells may be derived for example from blood samples which comprise immune cells (peritoneal, cerebral-spinal, pleural and/or synovial body fluids, lavage fluids from hollow organs (airways, lungs), homogenates and aspirates of lymph nodes, spleen, tonsils and/or other lymphatic tissue. The regulatory Th cells may also be obtained from animal tissues (e.g. from the spleen or the lymph nodes of an animal). The Th cells may also be part of a blood sample, e.g. from a test subject or human patient, particularly preferably from peripheral mononuclear blood cells (PBMC), body tissue or cells of tissue fluid.

Also provided are kits for practicing the methods of the invention. Kits may comprise a package with at least one container (e.g., vial) comprising an antibody for detecting CD154 for separating activated conventional T cells and instructions for such separation, as well as suitable buffers, labels, etc. The kit may also include reagents for separating an activated or non-activated regulatory Th cell based on antigens expressed by the cells, a number of examples of which are described herein (e.g. CD137, CD25). In some embodiments the marker is specific for regulatory T-cells (e.g., CD25+, GITR+ and CD127−). In some embodiments the marker that is specific for activated regulatory T-cells (e.g., CD137, latent TGF-beta (LAP), GARP (LRRC32) and CD121a/b). In some embodiments the kit comprises a first container containing antiCD154 and at least 1, at least 2, or at least 3 additional containers each containing an antibody that binds T-cells. In some embodiments each of the antibodies in the kit is differently labeled so that they can be distinguished.

It is preferred for the CD154 antibody in the kit to be coupled to a fluorescent substance, to a hapten or to magnetic microparticles.

A 4-1BB receptor antibody which is coupled to a fluorescent marker, a hapten or magnetic microparticles is provided for identifying and/or separating the activated, live regulatory Th cells. Fluorescent markers are known to the skilled worker, such as, for example, FITC, phycoerythrin (PE), allophycocyanin (APC), cascade yellow and peridinin chlorophyll protein (PerCP).

It is possible through use of the kit comprising a CD154 antibody coupled to a fluorescent marker, haptens or magnetic microparticles to identify and/or separate activated regulatory Th cells. Particularly preferred are the identification and/or separation of live, activated regulatory Th cells.

In this embodiment, the method of the invention can be used for example to identify and/or separate Th cells from a blood sample (or from a blood derivative) or from cell mixture derivatives of lymphatic organs or tumors of mammals.

The separated activated regulatory Th cells can be used before and/or after cloning and/or growing and/or concentrated in cell mixtures in and/or as pharmaceutical composition in the therapy or prevention of diseases. It is additionally possible for the coding gene sequences of the TCR (T-cell receptor) to be isolated from the separated regulatory T cells and be used for further therapeutic purposes such as, for example, for cellular therapies. It is additionally possible to employ the activated regulatory Th cells in the form mentioned in further investigations and/or analyses. The pharmaceutical composition can be used for the treatment and/or prevention of diseases in mammals, possibly including administration of a pharmaceutically effective amount of the pharmaceutical composition to the mammal.

The disease may be any disease, which can be treated and/or prevented through the presence of a separated cell and/or through increasing the concentration of the relevant cells in/at the relevant place, or in whole mammalian subjects and/or patients. The cell may be for example an activated regulatory Th cell, and the treated and/or preventively treated disease may be an autoimmune disease, an infectious disease, an allergy, transplant versus host disease (or allogeneic transplant rejection) and/or any other disease initiated by hypersensitivity.

Diseases for which the use set forth in the invention is particularly suitable are those arising through and/or during a lack of regulation of the immune response. These diseases may be transplant rejections, allergic conditions, certain infectious diseases and/or autoimmune diseases.

It is known in connection with autoimmune diseases that the immune system attacks endogenous structures, such as, for example, in rheumatoid arthritis, insulin-dependent Diabetes mellitus (IDDM), multiple sclerosis (MS), atherosclerosis, psoriasis, allogeneic stem cell transplantation, organ transplantation. A therapy with specific activated regulatory T cells is advantageous here. The goal in neoplastic diseases should be to eliminate regulatory T cells specific for tumor antigens so that the immune system can initiate efficient anti-tumor immune responses.

The invention also relates to the use of the composition of the invention and/or of the pharmaceutical composition of the invention for the treatment of diseases which are associated with a deficiency of cellular immunity, for example in the defect according to ICDIO code: D.84.4. Possibilities in this connection are septic disorders, inflammatory reactions and fever, autoimmune diseases and diseases of impairment of cell division such as, for example, cancer.

Accordingly, the invention also pertains to a method for treating one of the diseases mentioned herein using a highly pure population of activated Treg, as well as a method for preparing a medicament comprising a highly pure population of activated Treg for treating such diseases, as well as the use of a highly pure population of Treg for treating such diseases.

Inflammations in the sense of the invention are the reaction, borne by the connective tissue and the blood vessels, of the body to an externally or internally induced inflammatory stimulus with the purpose of eliminating or inactivating it and repairing the stimulus-related tissue damage. Inducing effects can be exerted by mechanical stimuli (foreign bodies, pressure, injury) and other physical factors (ionizing radiation, UV light, heat, cold), chemical substances (alkalis, acids, heavy metals, bacterial toxins, allergens and immune complexes) and pathogens (microorganisms, worms, insects) and pathological metabolic products, dysfunctional enzymes, malignant tumors. The event starts with a brief arteriolar constriction (through the action of adrenaline) with inadequate blood flow and tissue alteration, followed by the development of the classical local signs of inflammation (cardinal symptoms; according to GALEN and CELSUS), i.e. of redness (=rubor; dilation of vessels due to histamine), warmth (=calor; through a local increase in metabolism), swelling (=tumor; through escape of protein-rich liquid from the vessel walls which are altered—inter alia by histamine—, assisted by the slowed circulation of blood in the sense of prestasis to stasis), pain (=dolor; as a consequence of the increased tissue tension and pain-inducing inflammatory products, for example bradykinin) and functional impairment (=functio laesa). The process is supplemented by disturbance of the electrolyte balance (transmineralization), invasion of neutrophilic granulocytes and monocytes through the vessel walls (see also leukotaxis), the latter with the purpose of eliminating the inflammatory stimulus and damage to necrotic cells (phagocytosis); there is also invasion of lymphocyte effector cells which lead to the production of specific antibodies against the inflammatory stimulus (immune response), and eosinophils (in the healing phase or—very early—in the allergic-hyperergic event). The activation of the complement system brought about by the reaction releases fragments (C3a and C5a) of this system which—like histamine and bradykinin—act as mediators of the inflammation, specifically in the sense of stimulating the chemotaxis of the cited blood cells; there is also activation of blood clotting. This is followed by damage (dystrophy and coagulation necrosis) of the relevant organ parenchyma. The whole body responds depending on the intensity and nature of the inflammation with fever, stress, leucocytosis and alterations in the composition of plasma proteins (acute-phase reaction), which lead to an increased erythrocyte sedimentation rate. Preferred inflammations in the sense of the invention are the purulent, the exudative, the fibrinous, the gangrenous, the granulomatous, the hemorrhagic, the catarrhal, the necrotic, the proliferative or productive, the pseudomembranous, the serous, the specific or the ulcerative inflammations.

Autoimmune diseases in the sense of the invention are diseases partly attributable to the production of auto-antibodies and their harmful effect on the whole body or organ systems, i.e. auto-aggression. Autoimmune diseases may on the other hand also be diseases in which T cells possess a predominant role in the pathogenesis or initiation. Classification as organ-specific, intermediary and/or systemic autoimmune diseases is possible. Preferred organ-specific autoimmune diseases are Hashimoto's thyroiditis, primary myxedema, thyrotoxicosis (Basedow's disease), pernicious anemia, Addison's disease, myasthenia gravis and/or juvenile diabetes mellitus. Preferred intermediary autoimmune diseases are Goodpasture's syndrome, autoimmune hemolytic anemia, autoimmune leucopenia, idiopathic thrombocytopenia, pemphigus vulgaris, sympathetic ophthalmia, primary biliary cirrhosis, autoimmune hepatitis, ulcerative colitis and/or Sjogren's syndrome. Preferred systemic autoimmune diseases are rheumatoid arthritis, rheumatic fever, systemic lupus erythematosus, dermatomyositis/polymyositis, progressive systemic sclerosis, Wegener's granulomatosis, panarteritis nodosa and/or hypersensitivity angiitis. Typical autoimmune diseases are thyrotoxicosis, thyroid-related myxedema, Hashimoto's thyroiditis, generalized endocrinopathy, pernicious anemia, chronic gastritis of type A, diseases of single or all corpuscular elements of the blood (for example autoimmune hemolytic anemia, idiopath. thrombocytopenia or -pathy; idiopath. leucopenia or agranulocytosis), pemphigus vulgaris and pemphigoid, sympathetic ophthalmia and some types of uveitis, primary biliary cirrhosis of the liver and chronic aggressive autoimmune hepatitis, diabetes mellitus of type I, Crohn's disease and ulcerative colitis, Sjogren's syndrome, Addison's disease, lupus erythematosus disseminatus and as discoid form of this disease, as dermatomyositis and scleroderma, rheumatoid arthritis (=primary chronic polyarthritis), antiglomerular basement membrane nephritis. An aggressive immune response as a result of collapse of immunotolerance of self-determinants and a preponderance of inflammatory T-helper cells are the basis. The production of autoantigens is also possible, for example through host proteins combining with haptens (for example drugs), through ontogenetic tissue which develops only after development of self-tolerance and for protein components unmasked through changes in the conformation of the proteins in connection for example with infection by viruses or bacteria; also for new proteins which have arisen in connection with neoplasms first.

Septic diseases in the sense of the invention are disorders resulting from continuous or periodic invasion of pathogenic bacteria and/or their toxins from a disease focus and spread thereof via the lymph and blood to general or local infection.

Sepsis in the sense of the invention are preferably wound sepsis (phlegmone, thrombophlebitis, lymphangitis), puerperal sepsis (in puerperal fever), otogenic sepsis (in otitis media), tonsillogenic sepsis (in angina, peritonsilitis), cholangitic sepsis (in purulent cholecystitis, cholangitis), pylephlebitic sepsis (in pylephlebitis), umbilical sepsis (in omphalitis etc.), urosepsis and in dental granuloma. Sepsis in the sense of the invention may occur acutely to highly acutely (foudroyantly), subacutely (for example as endocarditis lenta) or chronically, but of course also as neonatal sepsis. Sepsis in the sense of the invention are therefore all pathogenic alterations in a patient which may be associated with intermittent fever and chills, and with spleen tumor, with toxic reactions or damage of the bone marrow or blood (polynuclear leukocytosis, anemia, hemolysis, thrombocytopenia) or else with pathogenic reactions on the heart and vasomotor nerves (tachycardia, centralization of the circulation, edemas, oliguria; possibly shock) or of the digestive tract (dry, coated tongue, diarrheas) or else with septicopyemia (pyemia with formation of septic infarctions and metastatic abscess).

Preferred disorders, which are associated with a deficiency of the cellular immune system are in the sense of the invention also: AIDS, acne, albuminuria (proteinuria), alcohol withdrawal syndrome, allergies, alopecia (hair loss), ALS (amyotrophic lateral sclerosis), Alzheimer's disease, AMD (age-related macular degeneration), anemia, anxiety disorders, anthrax, aortic sclerosis, arterial occlusive disease, arterial calcification, arterial occlusion, temporal arteritis, arteriosclerosis, arteriovenous fistulas, arthritis, arthrosis, asthma, respiratory failure, autoimmune disease, AV block, acidosis, prolapsed disc, peritonitis, pancreatic cancer, Becker's muscular dystrophy, benign prostatic hyperplasia (BPH), bladder carcinoma, hemophiliac, bronchial carcinoma, breast cancer, BSE, Budd-Chiari syndrome, bulimia nervosa, bursitis, Byler syndrome, bypass, chlamydial infection, chronic pain, cirrhosis, concussion, Creutzfeld-Jakob disease, bowel carcinoma, bowel cancer, intestinal tuberculosis, depression, diabetes insipidus, diabetes mellitus, diabetes mellitus juvenilis, diabetic retinopathy, Duchenne's muscular dystrophy, duodenal carcinoma, progressive muscular dystrophy, dystrophy, ebola, eczema, erectile dysfunction, obesity, fibrosis, cervical cancer, uterine cancer, cerebral hemorrhage, encephalitis, hair loss, hemolytic anemia, hemophilia, pet allergy (animal hair allergy), skin cancer, herpes zoster, myocardial infarction, heart failure, inflammation of heart valves, cerebral metastasis, stroke, brain tumor, testicular cancer, ischemia, Kahler's disease (plasmocytoma), infantile paralysis (poliomyelitis), bone atrophy, contact eczema, paralysis, cirrhosis of the liver, leukemia, pulmonary fibrosis, lung cancer, pulmonary edema, lymph node cancer (Hodgkin's disease), lymphogranulomatosis, lymphoma, lyssa, gastric carcinoma, carcinoma of breast, meningitis, anthrax, mucoviscidosis (cystic fibrosis), multiple sclerosis (MS), myocardial infarction, neurodermatitis, neurofibromatosis, neuronal tumors, renal cancer (renal cell carcinoma), osteoporosis, pancreatic carcinoma, pneumonia, polyneuropathies, potency impairments, progressive systemic sclerosis (PSS), prostate cancer, urticaria, transverse syndrome, traumatic, rectal carcinoma, pleurisy, craniocerebral trauma, vaginal cancer (vaginal carcinoma), sinusitis, esophageal cancer, tremor, tuberculosis, tumor pain, vaginal carcinoma, burns/scalds, poisonings, viral meningitis, menopause, soft tissue sarcoma, soft tissue tumor, impairments of cerebral blood flow and/or CNS tumors.

In a preferred embodiment, the cancer or the tumor which is treated or prevented is selected from the group of cancers or neoplastic diseases of the ear/nose/throat region, of the lung, of the mediastinum, of the gastrointestinal tract, of the urogenital system, of the gynecological system, of the breast, of the endocrine system, of the skin, bone and soft tissue sarcomas, mesotheliomas, melanomas, neoplasms of the central nervous system, cancers or neoplastic diseases in childhood, lymphomas, leukemias, paraneoplastics syndromes, metastases without known primary tumor (CUP syndrome), peritoneal carcinomatoses, immunosuppression-related malignancies and/or tumor metastases.

The tumors may be in particular of the following types of cancer: adenocarcinoma of the breast, of the prostate and of the colon; all types of lung cancer derived from the bronchia;

bone marrow cancer, melanoma, hepatoma, neuroblastoma; papilloma; apudoma, choristoma, branchioma; malignant carcinoid syndrome; carcinoid heart disease; carcinoma (for example Walker's carcinoma, basal cell carcinoma, basosquamous carcinoma, Brown-Pearce carcinoma, ductal carcinoma, Ehrlich's tumor, carcinoma in situ, Krebs-2carcinoma, Merkel cell carcinoma, mucous carcinoma, non-small cell bronchial carcinoma, oat cell carcinoma, papillary carcinoma, scirrhous carcinoma, bronchiole-alveolar carcinoma (bronchial carcinoma, squamous cell carcinoma and transitional cell carcinoma); histiocytic dysfunction; leukemia (for example in connection with B-cell leukemia, mixed cell leukemia, null cell leukemia, T-cell leukemia, chronic T-cell leukemia, HTLV II-associated leukemia, acute lymphocytic leukemia, chronic lymphocytic leukemia, master cell leukemia and myeloid leukemia); malignant histiocytosis, Hodgkin's disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma, myxoma, myxosarcoma; osteoma; osteosarcoma; Ewing's sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, choriablastoma; adenocarcinoma, adenoma; cholangioma; cholesteatoma; cylindroma; cystadenocarcinoma, cystadenoma; granulose cell tumor; gynadroblastoma; hidradenoma; islet cell tumor; leydig cell tumor; papilloma, sertoli cell tumor, theka cell tumor, leiomyoma; leiomyosarcoma; myoblastoma; myoma; myosarcoma; rhabdomyoma; rhabdomyosarcoma; ependynoma; ganglioneuroma, glioma; medulloblastoma, meningioma; neurilemmonoma; neuroblastoma; neuroepithelioma, neurofibrona, neuroma, paraganglioma, non-chromaffin paraganglioma, angiokeratoma, angiolymphoid hyperplasia with eosinophilia; sclerosieren angiomas; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phyllodes; hemangiosarcoma; lymphangiosarcoma; myxosarcoma, ovarian carcinoma; sarcoma (for example Ewing's sarcoma, experimentally, caposi sarcoma and master cell sarcoma); neoplasms (for example bone neoplasms, breast neoplasms, neoplasms of the digestive system, colorectal neoplasms, liver neoplasms, pancreatic neoplasms, pituitary neoplasms, testicular neoplasms, orbital neoplasms, neoplasms of the head and neck, of the central nervous system, neoplasms of the hearing organ, of the pelvis, of the respiratory tract and of the urogenital tract); neurofibromatosis and cervical squamous cell dysplasia.

In a further preferred embodiment, the cancer or the tumor which is treated or prevented is selected from the group: tumors of the ear nose and throat region including tumors of the inner nose, of the paranasal sinuses, of the nasopharynx, of the lips, of the oral cavity, of the oropharynx, of the larynx, of the hypopharynx, of the ear, of the salivary glands and parangliomas, tumors of the lung including non-small cell bronchial carcinomas, small cell bronchial carcinomas, tumors of the mediastinum, tumors of the gastrointestinal tract including tumors of the esophagus, of the stomach, of the pancreas, of the liver, of the gall bladder and of the biliary tract, of the small bowel, colon and rectal carcinomas and anal carcinomas, urogenital tumors including tumors of the kidneys, of the uretas, of the bladder, of the prostate, of the urethra, of the penis and of the testis, gynecological tumors including tumors of the cervix, of the vagina, of the vulva, corpus carcinoma, malignant trophoblastic disease, ovarian carcinoma, tumors of the uterine tube (tuba faloppii), tumors of the abdominal cavity, carcinomas of the breast, tumors of endocrine organs including tumors of the thyroid, of the parathyroid, of the adrenal cortex, endocrine pancreatic tumors, carcinoid tumors and carcinoid syndrome, multiple endocrine neoplasms, bone and soft tissue sarcomas, mesotheliomas, skin tumors, melanomas including cutaneous and intraocular melanomas, tumors of the central nervous system, tumours in childhood including retinoblastoma, Wilm's tumor, neurofibromatosis, neuroblastoma, Ewing's sarcoma tumor family, rhabdomyosarcoma, lymphomas including non-Hodgkin lymphomas, cutaneous T-cell lymphomas, primary lymphomas of the central nervous system, Hodgkin's disease, leukemias including acute leukemias, chronic myeloid and lymphatic leukemias, plasma cell neoplasms, myelodysplastic syndromes, paraneoplastic syndromes, metastases without known primary tumor (CUP syndrome), peritoneal carcinomatosis, immunosuppression-related malignancy including AIDS-related malignancies such as Kaposi's sarcoma, AIDS-associated lymphomas, AIDS-associated lymphomas of the central nervous system, AIDS-associated Hodgkin's disease and AIDS-associated anogenital tumors, transplantation-related malignancies, metastatic tumors including brain metastases, lung metastases, liver metastases, bone metastases, pleural and pericardial metastases and malignant ascites.

In a further preferred embodiment, the cancer or the tumor which is treated or prevented is selected from the group including cancers or neoplastic diseases of the carcinomas of the breast, of the gastrointestinal tumors, including colon carcinomas, gastric carcinomas, pancreatic carcinomas, colon cancer, small bowel cancer, of the ovarian carcinomas, of the cervical carcinomas, lung cancer, prostate cancer, renal cell carcinomas and/or liver metastases.

Immunopathological reactions cause the loss of function of a particular tissue and may destroy tissues. The use according to the invention allows active regulatory Th cells to be isolated from patients with these diseases in order to treat the tissue-damaging immune response. In the case of neoplastic diseases, the use according to the invention is intended to make it possible to specifically eliminate tumor-specific Treg in vitro or ex vivo. If the activated regulatory Th cells are present in too small a number, they can be separated and concentrated and/or grown in cell cultures. In both cases, the patient could be treated with the concentrated and/or grown and thus increased number of regulatory Th cells, which would lead to the expectation of suppression of the immunopathological response and thus an improvement and/or cure of the disease. Autoimmune diseases for which CD137 could be used as marker for identifying and/or isolating and subsequently concentrating active regulatory Th cells and would be expected to be a successful therapy include, but are not restricted only thereto, diabetes mellitus (IDDM), multiple sclerosis (MS), atherosclerosis (AS), psoriasis, inflammations of the bowel, autoimmune-related hemolytic anemia, Sjogren's syndrome, autoimmune-related thyroiditis and systemic lupus erythematosis.

The skilled worker is aware that regulatory Th cells are able in connection with transplantations to suppress an immune response, which might lead to transplant rejection. Treatment of a patient and/or subject with initially isolated and then concentrated specifically activated regulatory Th cells might prevent and/or impede transplant rejection. Transplant rejections are induced by an immune response of the transplant acceptor. In this case, the immune cells of the acceptor attack the exogenous tissue. In this form of use, Th cells of the target patient would be exposed in vitro to cells, cell extracts, isolated antigens or proteins of the organ donor before or after the transplantation. After this, the active regulatory Th cells would, after an appropriate growing time, be identified and/or separated by means of the CD137 marker. The regulatory Th cells identified and/or separated by using the method of the invention would then be returned to (i.e., administered to) the transplant acceptor. The result thereof is that the cells treated by this method suppress the immune response to the transplant, and the transplant rejection is delayed or prevented. Use of the CD137 marker might be employed inter alia for allogeneic transplants and/or heterotransplants such as, for example, for transplantations of the heart, lungs, bowel, cornea, kidneys and bone marrow.

In the case of an allergy, regulatory Th cells would be identified and/or separated either before the polyclonal activation of the T cells or after culturing with specific allergens. The identified and/or separated cells would then be returned, after a possible propagation, to the patient. It is then expected that the regulatory Th cells treated in this way will suppress the immune response, and the symptoms correlating with the antigens used will improve.

The treatment of allergies by means of identifying and/or isolating active regulatory Th cells with the CD137 marker and the described method would be suitable inter alia for skin rashes, atopic dermatitis, asthma, allergic rhinitis, insect toxins and food allergy such as, for example, toward gluten, dairy products, nuts and/or fish antigens.

In the case of infectious diseases it is important to strengthen the immune response than to weaken it. In certain diseases it is appropriate to modulate the immune response in order to alter the progression of the disease. Such cases of modulation occur in diseases where immunopathological reactions occur through the infection and destroy tissue, and in those where the immune response does not protect the body. It would be possible through the identification and/or isolation of active regulatory Th cells to suppress the immune response and ameliorate and/or prevent immunopathological damage.

A further alternative would be treatment with regulatory Th cells, which have been isolated from a patient and exposed to particular antigens in order to obtain regulatory Th cells which could redirect the immune response in a defined, particular direction.

Genes can be introduced into the cells before culturing or transplantation for a diversity of purposes, e.g. in order to prevent or reduce the susceptibility to an infection, to replace genes which are subject to a loss of a functional mutation, to increase the ability of the Treg to inhibit Th cells etc. It is moreover possible to introduce vectors, which express antisense mRNA or ribozymes, thus blocking the expression of an unwanted gene. Other methods of gene therapy are the introduction of drug-resistance genes, for example the drug-resistance gene (MDR) or antiapoptosis genes such as bcl-2. A further possibility is to use techniques known to the skilled worker for transfecting target cells, e.g. by electroporation, calcium-precipitated DNA, fusion, transfection or lipofection. The particular way in which the DNA is introduced is not crucial for use of the invention.

The skilled worker is aware of many vectors, which can be used in order to transfer exogenous genes into mammalian cells. The vectors may be episomal, e.g. plasmids, virus vectors such as, for example, cytomegalovirus, adenovirus etc. The genes can also be integrated into the target cell genome by homologous recombination or by random integration, such as, for example, vectors derived from retroviruses such as MMLV, HIV-1, ALV, etc.

Active factors of the Treg cells can be analyzed by means of in vitro assays or screenings. It is also possible to carry out co-culture assays in order to study the alterations in Tregs, which suppress the multiplication of normal T cells including CD4 T and CD8 T. Interactions with dendritic cells and other antigen-determined cells can likewise be investigated. The regulatory cells separated according to the invention can be the starting material for a large diversity of different analyses, e.g. of immunoassays for protein-binding studies, determinations of cell growth, differentiation and functional activity, production of hormones etc.

EXAMPLES

The present invention is described in more detail through the following examples, which are not limiting to the invention.

Example 1

FIG. 1: Shortly after stimulation, a large fraction of the CD137+ Treg also expressed CD154. Peripheral Th-cells (A) were isolated using FACS or MACS from PBMC and were cultivated with allogeneic monocyte-derived dendritic cells (moDC) for 0 to 20 hours. At the time points indicated, the expression of CD137 versus CD154 was determined using flow-cytometry. After 8 hours, already 20% of the CD137+ T-cells also expressed CD154. After 16 hours, at which the maximum CD137 expression is detected, 30% of the cells are also positive for CD154. This shows that, contaminating T-cells are already present at early time points, but that the maximum number of target cells expresses a marker only after 16 hours. The contaminating cells can be depleted by the method of the invention.

Example 2

Figure 2A:
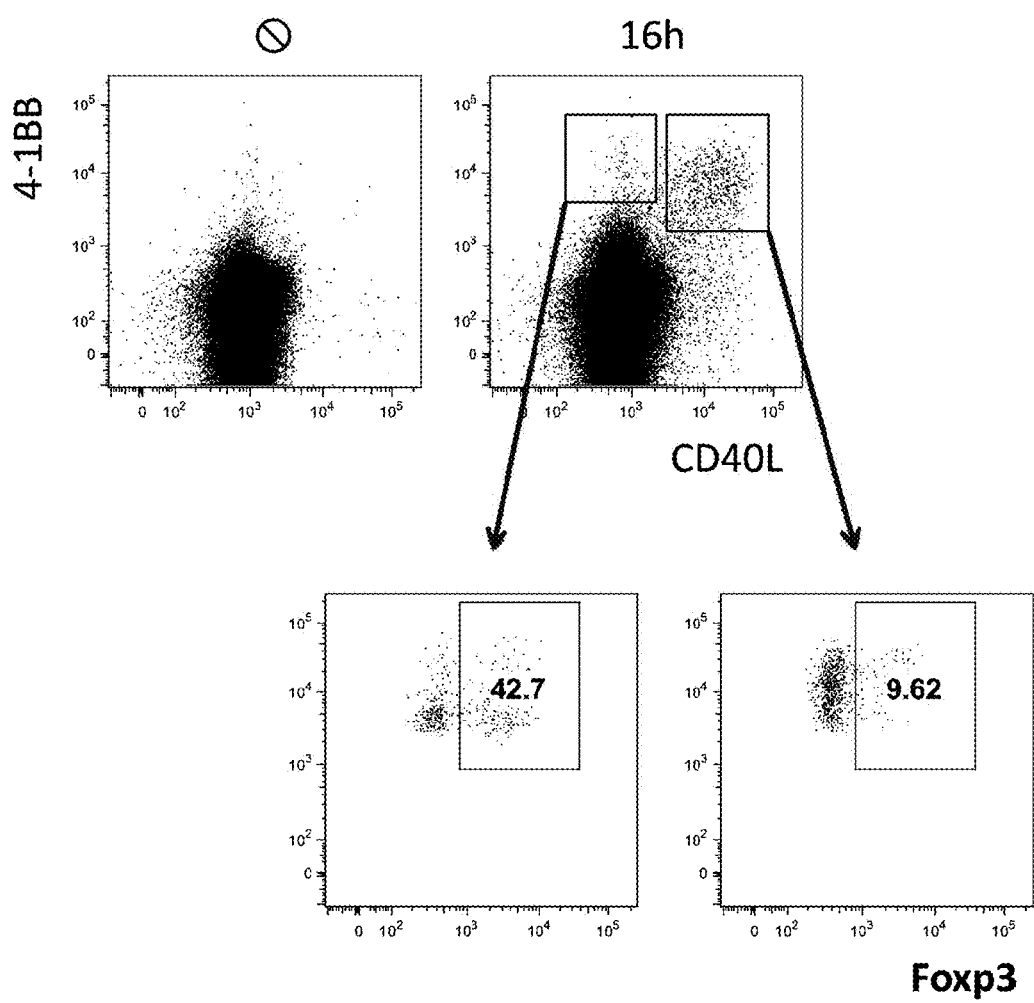
FIG. 2 shows that within the CD137+ T-cells mixture CD154 T-cells express more FoxP3.
Figure 2B:
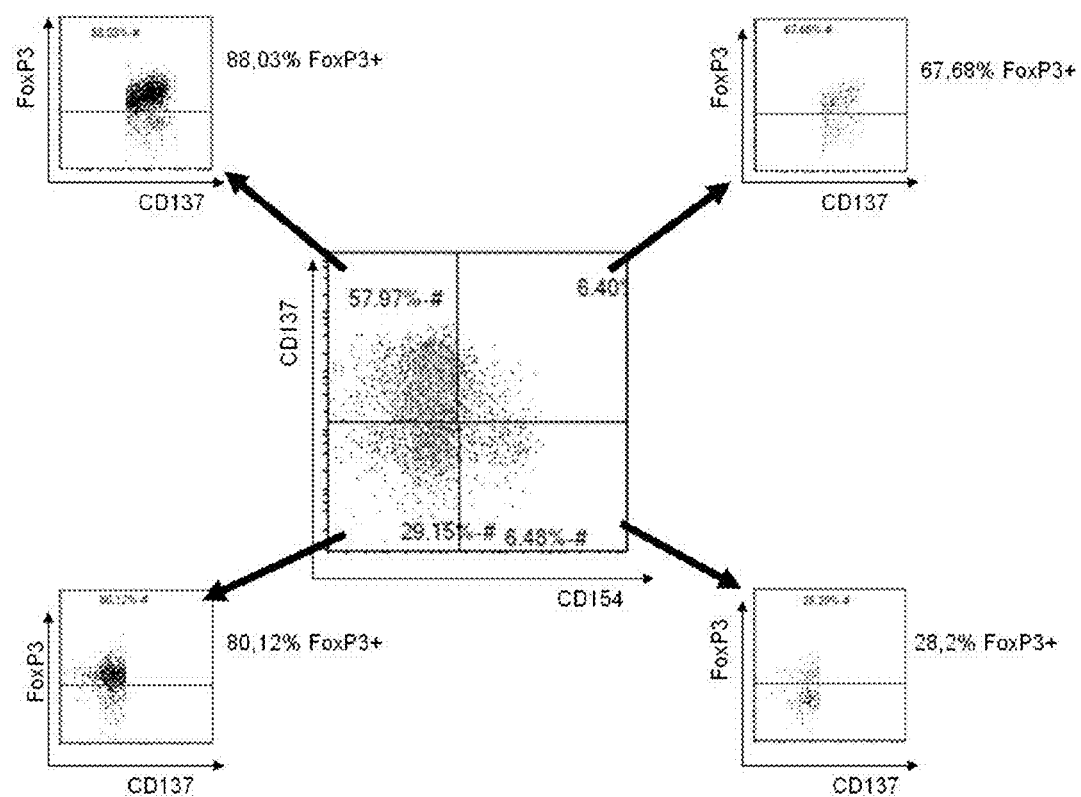

FIG. 2: Within the CD137$^+$ T-cells mixture, CD154$^-$ T-cells isolated according to the method of the invention express more FoxP3.

FIG. 2(A) Peripheral Th-cells were isolated from PBMC using FACS or MACS and/or cultivated for 16 hours with allogeneic monocyte-derived dendritic cells (moDC). The expression of CD137 versus CD154 was determined using flow-cytometry. Using FACS sorting, CD137+ cells were separated into CD154 positive and negative cells and were stained intercellular against FoxP3. 80% of the FoxP3 positive cells are part of the CD137+CD154− fraction, whereas the CD137+CD154+ fraction consists to 90% of FoxP3$^-$ conventional T-cells.

FIG. 2 (B) Alternatively, Treg was isolated using the "MACS Treg isolation Kit" and was stimulated polyclonally with MACSiBeads loaded with CD3/CD28 for 6 hours. Subsequently, CD137 and CD154 as well as the expression of FoxP3 was determined and correlated to each other. Even after polyclonal stimulation, the CD137+ CD154− Treg contain high frequencies of FoxP3 positive Treg, whereas, e.g., CD154 single positive Treg show very low frequencies of FoxP3+ Treg.

Example 3

Figure 3:
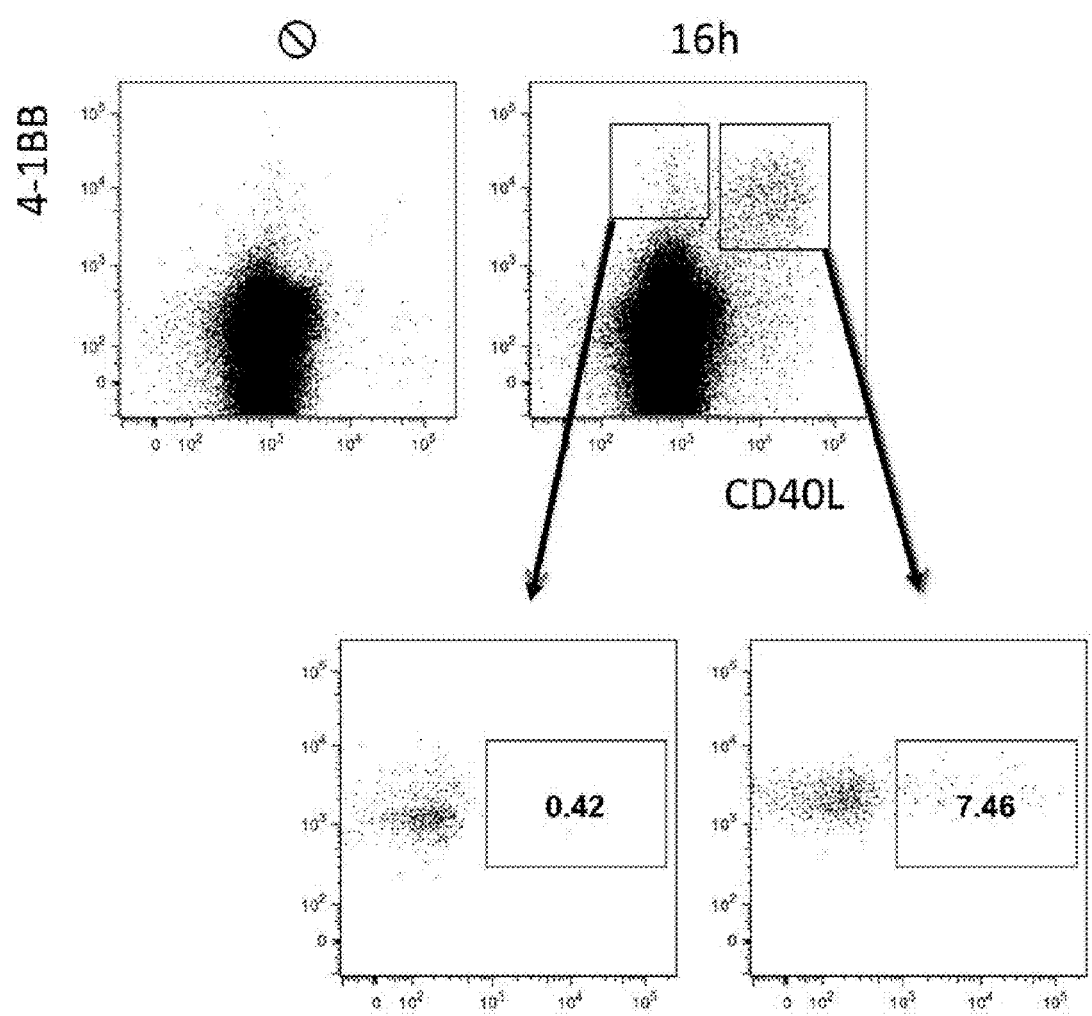
FIG. 3 shows that within the CD137+ T-cell mixture only CD154+ T-cells express effector cytokines.

FIG. 3: Within the CD137+ T-cell mixture, only CD154+ T-cells express effector cytokines. T-cells expressing effector cytokines are undesirable and can be depleted with the method of the invention. Peripheral Th-cells were isolated using FACS or MACS and were cultivated for 16 hours with allogeneic monocyte-derived dendritic cells (moDC). The expression of CD137 versus CD154 was determined using flow-cytometry. Using FACS, CD137+ was separated into CD154 positive and negative cells and were stained intracellularly against IFN-gamma.

Example 4

Figure 4:
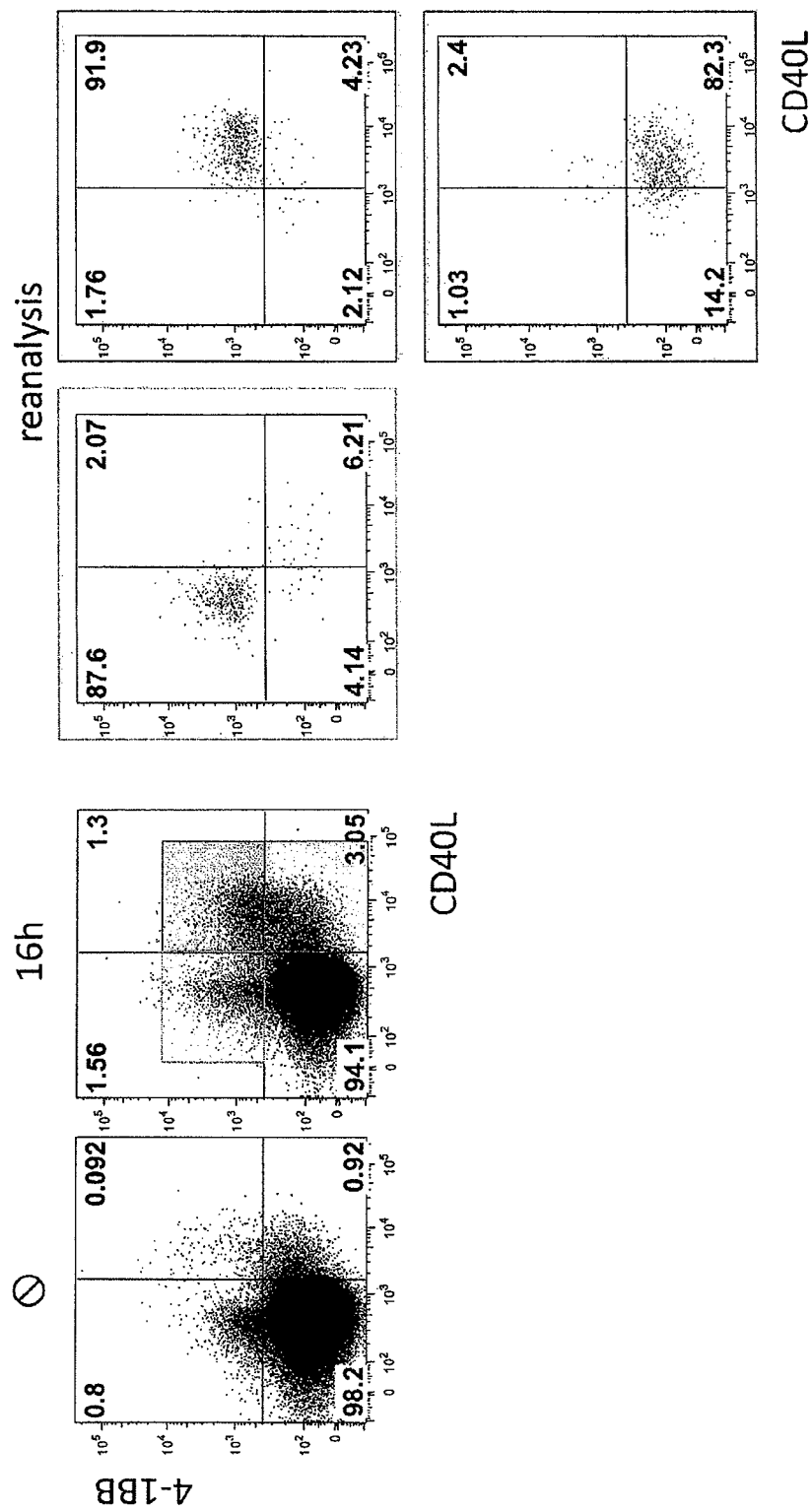
FIG. 4 shows the time window for sorting and reanalysis of CD137/CD154 double- and single-positive T-cells.
Figure 5:
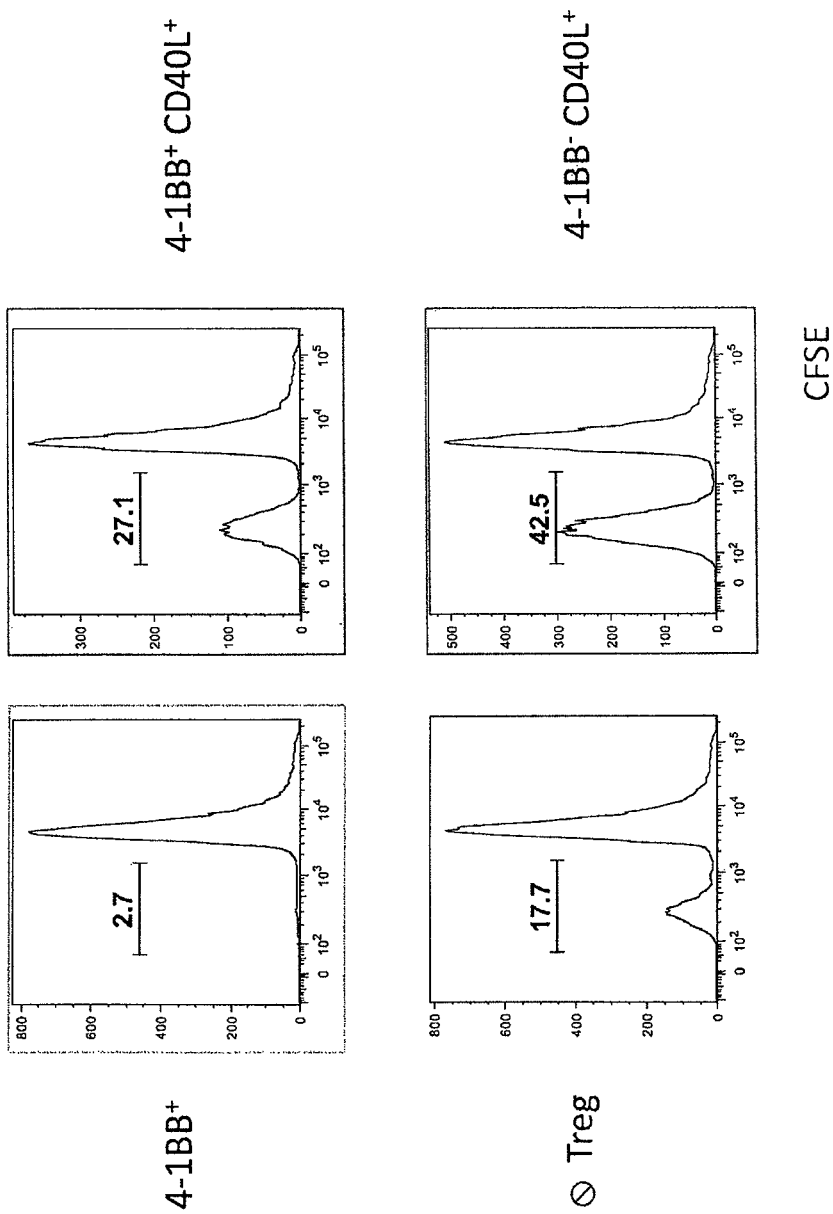
FIG. 5 shows that only CD154– Treg cells show suppressive properties.

FIG. 4 and FIG. 5 show that the combined use of CD154 (depleting CD154+) and CD137 (enriching CD 137+) allows the isolation of activated Treg even at late timepoints of stimulation.

FIG. 4: Time window for sorting and reanalysis of CD137/CD154 double- and single-positive T-cells. Peripheral Th-cells were isolated from PBMC using FACS or MACS and were cultivated for 16 hours with allogeneic monocyte-derived dendritic cells (moDC). The expression of CD137 versus CD154 was determining using flow-cytometry. Using FACS, CD137+ CD154−, CD137+ CD154+, and CD137− CD154+ T-cells were separated and were tested in an individual suppression assay for suppressive properties (see FIG. 4).

FIG. 5: Only CD154− Treg cells show suppressive properties. The sorted T-cell populations shown in FIG. 4 were co-incubated with naive CFDA marked T-cells (1:10 Treg: naive) and was stimulated with allogeneic moDC (1:20 DC:T) for 4 to 6 days. The proliferation (CFDA loss) of the naive target cells is shown. In the presence of CD154- depleted Treg, the proliferation in respect to alloantigen DC is completely inhibited, whereas in the presence of CD154+ T-cells, a strong proliferation occurs.

Example 5

Figure 6:
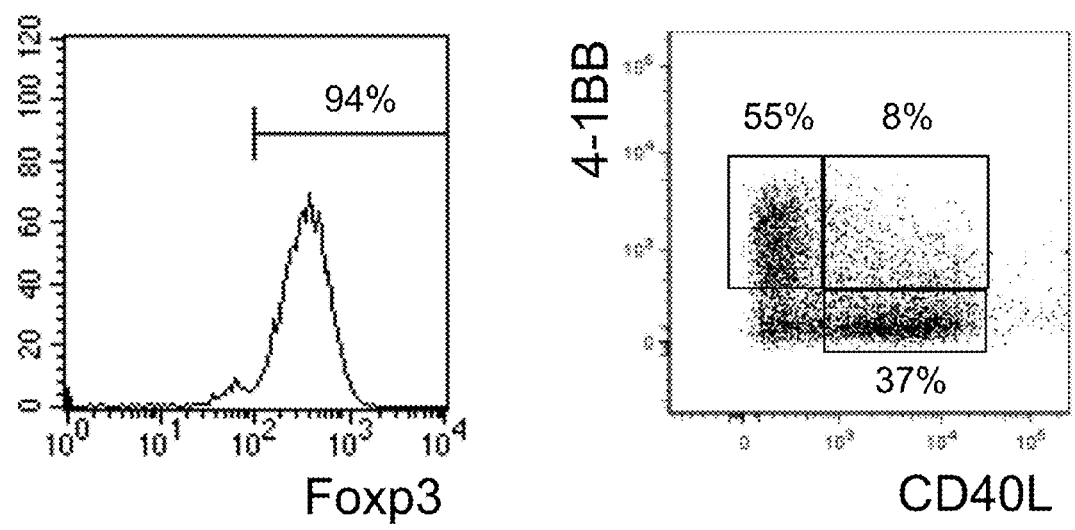
FIG. 6 shows that CD25++ FoxP3+ Treg contain CD154+ T-cells.
Figure 7:
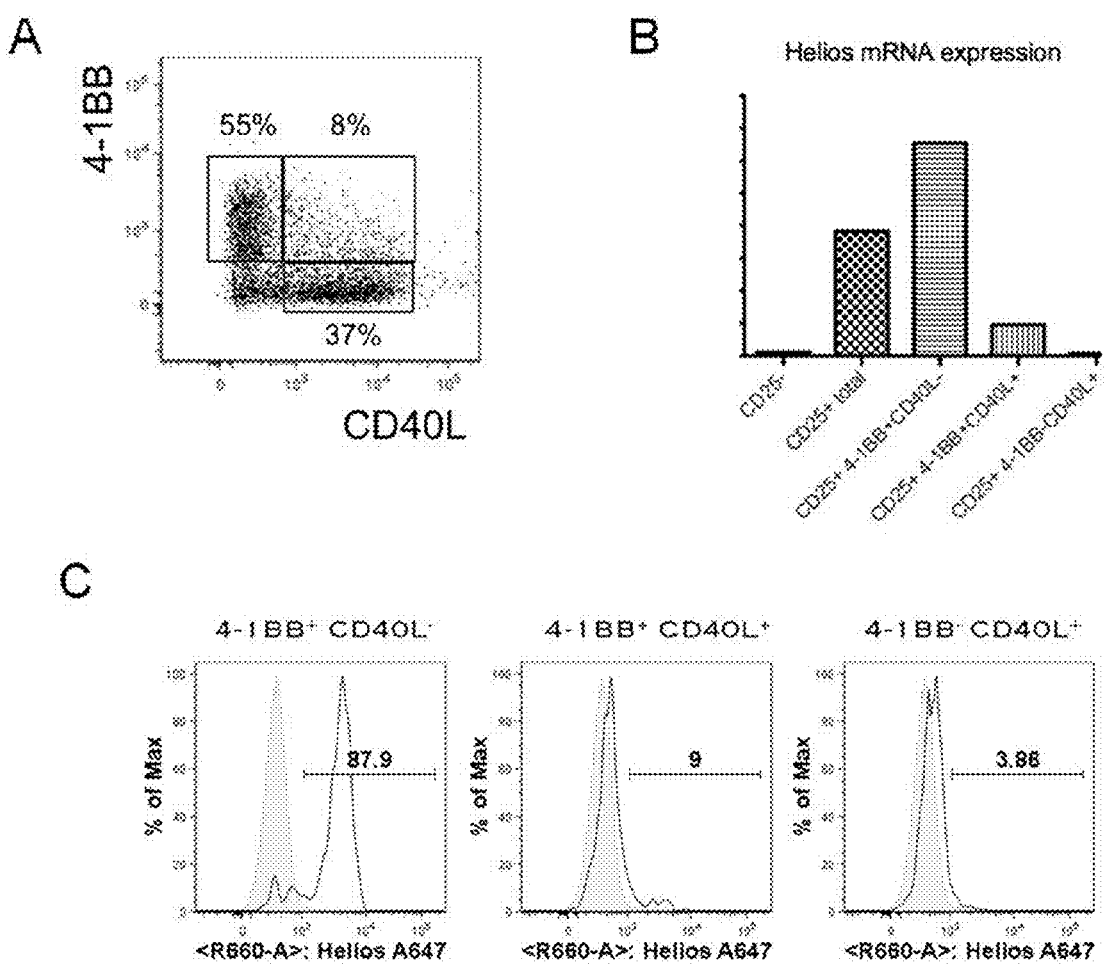
FIG. 7 shows that Helios is almost exclusively expressed by CD137+CD154– Treg.
Figure 8:
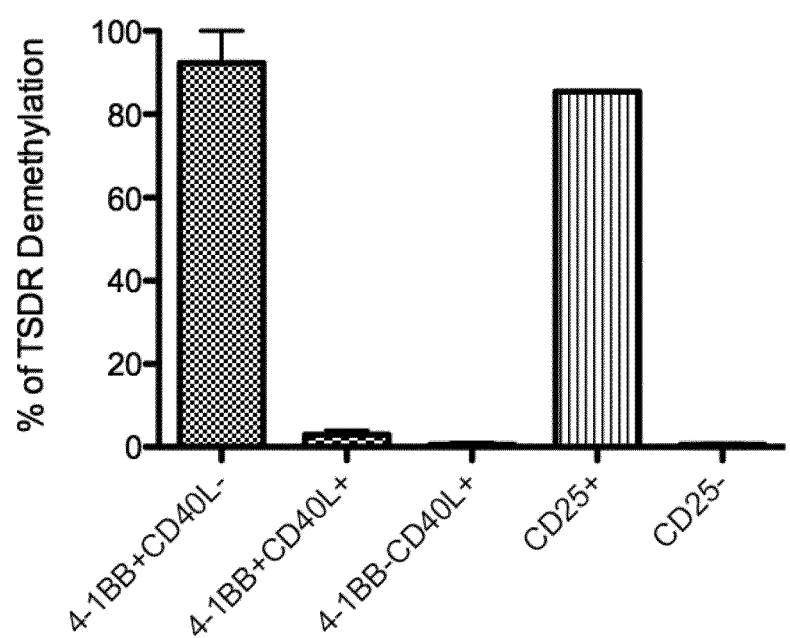
FIG. 8 shows that CD137+ CD154– Treg show strong de-methylation of the FoxP3 promoter.

FIGS. 6-8 demonstrate that the CD137+ T cells which co-express CD154 also contain Foxp3+ T cells. However, these CD154+ Foxp3+ T cells in contrast to their CD154− counterparts do not represent true Treg with stable expression of Foxp3 as they do not express the transcription factor Helios and they show no demethylation of the Foxp3 gene. This indicates that CD154 can be used as a discrimination marker between stable Treg and Treg which do not show stable regulatory phenotype and therefore may be less useful for application in Treg based therapies.

FIG. 6: CD25++ FoxP3+Treg contain CD154+ T-cells. CD4+ Treg were sorted from PBMC using FACS based on the strong expression of CD25 with a high purity (94% FoxP3+). Subsequently, the cells were stimulated polyclonally with PMA/ionomycin and were stained for CD137 and CD154. As can be seen in the figure, highly purified Treg contain up to 45% CD154+ cells, which in part also expressed CD137.

FIG. 7: Helios is almost exclusively expressed by CD137+CD154− Treg. Helios is a transcription factor that is expressed by Treg that were generated "naturally" in the thymus but not by Treg that are "induced" in the periphery (Thornton et al., J. Immunol. 2010 184(7): 3433-41). The polyclonally activated Treg shown in FIG. 6 were sorted according to CD154 and CD137 expression (FIG. 7A) and were examined for the four different populations of helios mRNA (FIG. 7B). Analogously, the helios protein expression in T-cells was determined in CD137/CD154 single- or double-producers that were activated for 16 hours with allo-DC through intracellular staining (FIG. 7C). As shown, helios mRNA and protein is almost exclusively expressed by CD137+ CD154− Treg, whereas FoxP3+ CD154+ Treg express no helios.

FIG. 8: CD137+ CD154− Treg show strong de-methylation of the FoxP3 promoter. CD4 T-cells were stimulated with allo-DC for 16 hours and CD137 and/or CD154 single/double-positive cells were sorted. Of the sorted cells, the de-methylation of CpG motives in the promoter region of the FoxP3 gene was analyzed (TSDR region). Demethylation in these regions is an indication of stable expression of FoxP3 and therefore of stable Treg identity (Baron et al Eur J Immunol. 2007 37(9):2378-89). As shown in the figure, de-methylation of the FoxP3 promoter was found exclusively in CD154− CD137+ Treg and not in CD154+ cells.

Example 6

Figure 9:
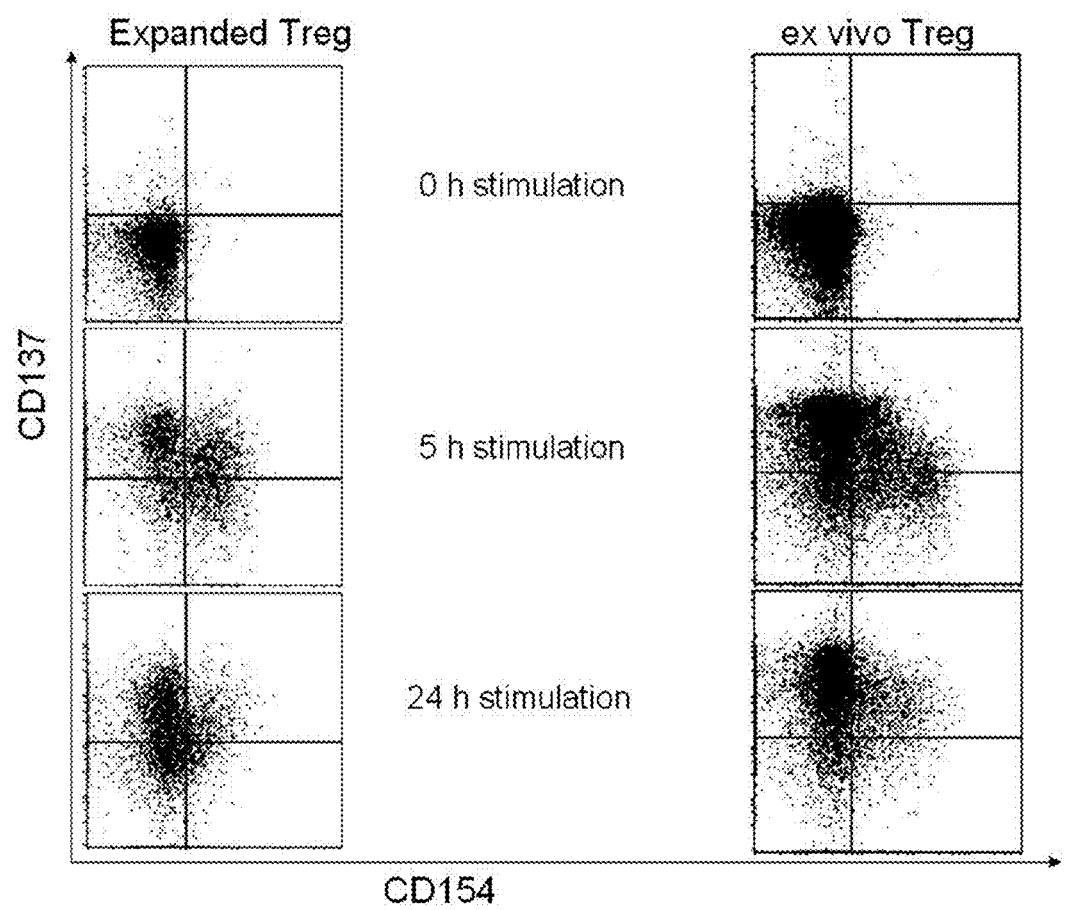
FIG. 9 shows that CD137 and CD154 are also expressed on expanded Treg from various populations.

FIG. 9: CD137 and CD154 are also expressed on expanded Treg from various populations. Description of the figure: Human Treg were purified from PBMC with the "CD127—Treg Isolation Kit" (Miltenyi Biotec GmbH) and were expanded using CD3/CD28-loaded magnetic particles (Treg MACSiBeads) for 14 days. Subsequently, the Treg were stimulated for the time periods indicated using Treg MACSiBeads and were stained for CD137 and CD154. Both, CD137 and CD154 single- and double-positive Treg were identified.

Example 7

FIG. 10: Depletion of CD154+ Treg from a Treg expansion culture increases the FoxP3 purity and the long terms stability of FoxP3 expression.

Figure 10A:
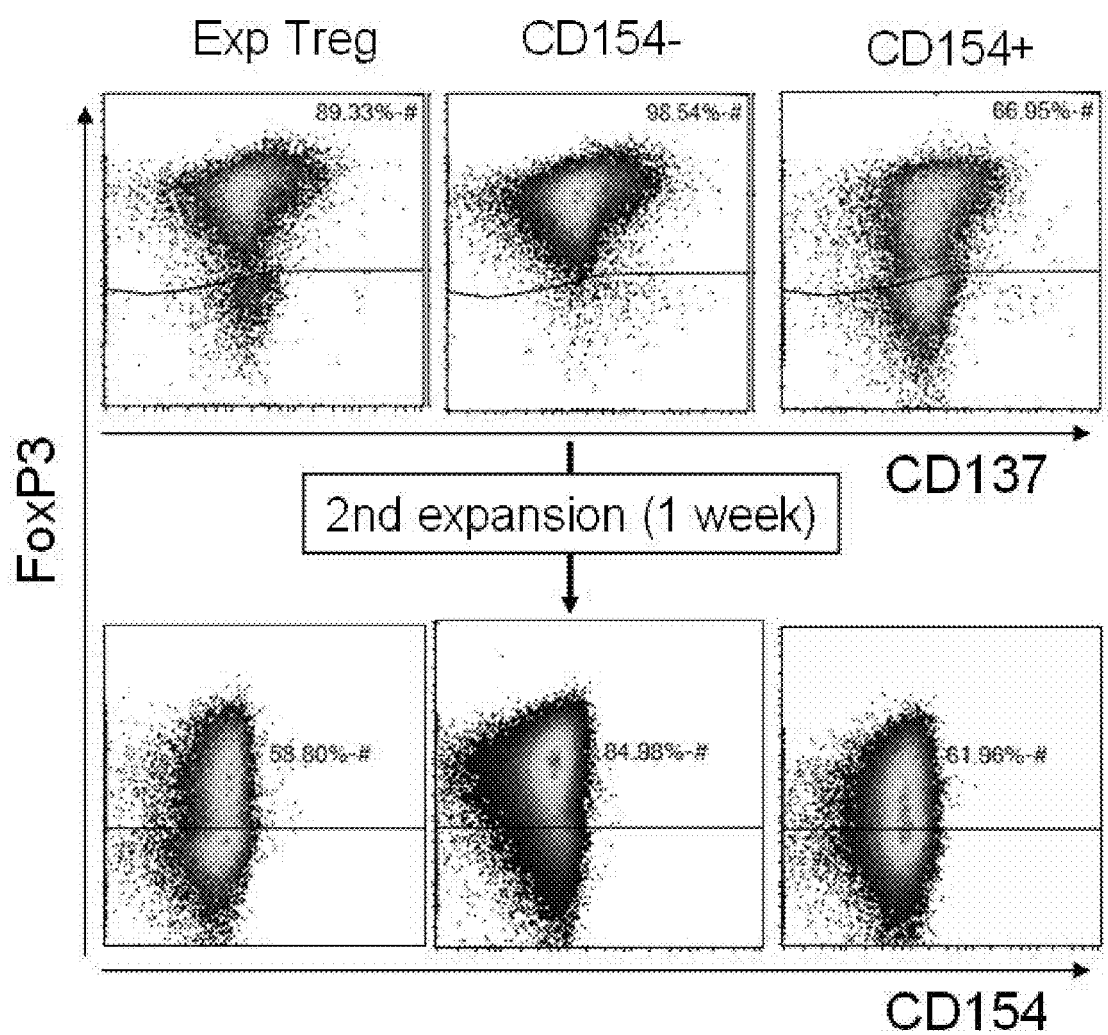
FIG. 10 shows that depletion of CD154+ Treg from a Treg expansion culture increases the FoxP3 purity and the long terms stability of FoxP3 expression.

FIG. 10A: CD127− Treg were expanded for 14 days using Treg CD3/CD28 MACSiBeads and subsequently restimulated for 6 hours with Treg MACSiBeads. After 6 hours, the MACSiBeads were removed and subsequently, CD154+ Treg were separated through magnetic depletion (MACS). The separated populations were then expanded in vitro for another 6 days with Treg MACSiBeads and then FoxP3 expression was again measured using FACS. As shown, through depletion of CD154+ Treg a) the purity of FoxP3 is increased, and b) even after repeated expansion, a higher concentration of FoxP3 is obtained, which indicates that non-Treg and non-stabile Treg can be separated through CD154 depletion.

Figure 10B:
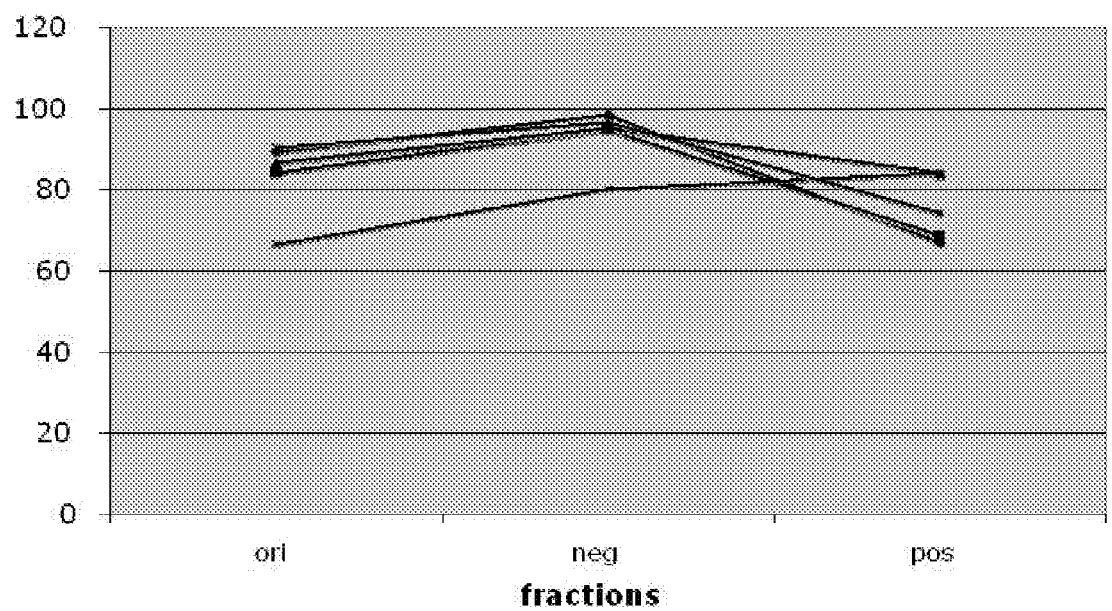

FIG. 10B: Effect of CD154 depletion on FoxP3 purity in five different donors. Treg of five healthy donors were expanded as described above, and the FoxP3 expression was determined before and after CD154 depletion. The data show that CD154 depletion is suited for removing contaminating effector cells even from cultures of highly purified Treg.

Example 8

Obtaining polyclonal regulatory T-cells for treatment of autoimmunity, organ transplant rejection and chronic inflammations Regulatory T-cells can be obtained from human biological material, like blood, PBMC, leukapheresis, tissue samples either directly or by enriching the cells with a general marker for regulatory T-cells (e.g. using CliniMACS (Miltenyi Biotec GmbH) Isolation of CD25+ cells with or without prior depletion of other cells (CD127+, CD8, CD19)).

The mixture thus obtained can then further be purified through stimulation of T-cells, using all known antigens (e.g.

CD3/CD28 antibody coupled to macroscopic carrier materials, super antigens), which elicit a polyclonal activation of all T-cells (the stimulation of $10^5$-$5\times10^{10}$ cells is performed in cell culture medium, circa $10^5$-$10^7$ cells per ml, at 37° C.). Stimulants are added in the usual concentrations, (e.g. magnetic particles "MACSiBeads" (Miltenyi Biotec GmbH) loaded with CD3/CD28 can be used that are mixed with the T-cells in a ratio of between 1:10 to 10:1) and the stimulation may last from 2 to 24 hours.

After stimulation of, for example, 2 to 24 hours, CD154 positive T-cells can be separated from the mixture by labeling the cells, for example, using magnetic microparticles coupled to CD154 specific antibodies and removing them from the mixture using a magnetic separation column, thereby obtaining purified activated Treg.

Additionally, markers for activated Treg can be used (e.g. CD137, latent TGF-beta (LAP), GARP (LRRC32), CD121a/b) in order to enrich subsequently activated Treg further, e.g. through magnetic cell sorting or FACS sorting.

The CD154 negative or CD154 negative/CD137 positive Treg can be applied directly to a patient or can be expanded in a cell culture, for example with polyclonal T-cell stimulation methods. This procedure can be repeated at any time point of the expansion culture in order to further improve the purity and to remove eventually conventional T-cells that might have expanded also.

Example 9

Obtaining antigen-specific Treg. A further use of the invention is the purification of antigen-specific Treg. For this use, un-separated T-cells, e.g. PBMC, leukapheresis, tissue samples, separated T-cells or Treg, which have been pre-enriched following another method (e.g. magnetic separated CD25+ cells), are brought into contact with a specific antigen (proteins, peptides, antigen-loaded antigen presenting cells (APC), allogeneic APC, etc.) for 2 to 24 hours. A person of skill in the art is aware of how the bringing into contact can be performed in various concentrations, media, and cell density. An example is the co-culture of T-cells with allogeneic APC (for example, from monocyte-generated dendritic cells or other allogeneic dendritic cells) in a ratio of T:DC 1:1-20:1 with a cell density of between $10^5$-$10^7$ cell per ml.

Subsequently, using labeling with specific antibodies that are coupled with magnetic particles, unwanted activated conventional T-cells can be removed by removing CD154+ cells using a magnetic separation column (for example, CliniMACS (Miltenyi Biotec GmbH)). Antigen-specific Treg can be obtained with high purity through subsequent enrichment via a molecule that is specific for activated Treg (for example, CD137, latent TGF-beta (LAP), GARP (LRRC32), CD121a/b). This can also be achieved through labeling with specific antibodies (0.1 to 20 mg/ml) that are coupled to magnetic microparticles, where an enrichment can be achieved again using a magnetic separation column (for example, CliniMACS (Miltenyi Biotec GmbH)). Alternatively, fluorochrome marked antibodies can also be used, in which case the removal may be performed using fluorescent activated cell sorting.

The purified Treg can be applied directly to a patient or optionally expanded in culture or further activated. This procedure can be repeated at any time point in the culture or can be combined with the purification described above after polyclonal stimulation in order to increase the purity of the culture. Antigen-specific Treg have a selective suppressing activity on immunoreactions against these specific antigens and are therefore particularly well suited to treat all immunoreactions (autoantigens), rejection of transplants (alloantigens) or other immune diseases involving reactions against specific antigens.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

All publications and patent documents cited herein are incorporated herein by reference as if each such publication or document was specifically and individually indicated to be incorporated herein by reference. Citation of publications and patent documents is not intended as an indication that any such document is pertinent prior art, nor does it constitute any admission as to the contents or date of the same.

The invention claimed is:

1. A method of producing a pharmaceutical composition comprising an enriched cell population of activated regulatory T-cells not expressing CD154, the method comprising:
   (A) preparing said enriched cell population by a process that comprises:
      (1) obtaining a cell mixture comprising activated T-cells, the mixture containing both activated regulatory T-cells and other T-cells;
      (2) contacting the cell mixture with a molecule that specifically binds CD154;
      (3) separating and recovering cells from the mixture that have not bound to the molecule in step (2); and
      (4) further enriching the cells for expression of at least one additional marker that is different from CD154 and is specifically present on regulatory T-cells or activated regulatory T-cells by contacting the cell mixture with a molecule that specifically binds the additional marker and recovering cells that have bound thereto, wherein step (4) is conducted before the contacting of step (2) or during or after the separating step of step (3); and
   (B) formulating the enriched cell population prepared according to step (A) as a pharmaceutical composition suitable for administration to a human subject;
   thereby producing a pharmaceutical composition comprising an enriched population of activated regulatory T-cells not expressing CD154.

2. The method of claim 1, wherein the process for preparing the enriched cell population comprises:
   (a) contacting the cell mixture comprising activated T-cells with a first molecule that specifically binds CLD154;
   (b) depleting CD154 positive T-cells from the mixture by recovering cells that have not bound to the first molecule following step (a);
   (c) contacting the cells from step (b) with a second molecule that specifically binds an additional marker that is different from CD154 and is specifically expressed on regulatory T-cells or activated regulatory T-cells;
   (d) positively selecting cells that bind to the second molecule in step (c); and (e) recovering cells that have bound the second molecule but not the first, thereby producing the enriched cell population.

3. The method of claim 1, wherein the process for preparing the enriched cell population comprises:
   (a) contacting the cell mixture comprising activated T-cells with a first molecule that specifically binds an additional marker that is different from CD154 and is specifically expressed on regulatory T-cells or activated regulatory T-cells;
   (b) positively selecting cells that bind to the first molecule in step (a);
   (c) contacting cells selected in step (b) with a second molecule that specifically binds CD154;
   (d) depleting CD154 positive T-cells that have bound the second molecule in step (c); and
   (e) recovering cells that have bound the first molecule but not the second, thereby producing the enriched cell population.

4. The method of claim 1, claim 2 or claim 3, wherein the additional marker is selected from CD25 and GITR.

5. The method of claim 1, claim 2 or claim 3, wherein the additional marker is selected from CD137, latent TGF-beta (LAP), GARP (LRRC32) and CD121a/b.

6. The method of claim 1, wherein the molecule binding CD154 is an antibody or antibody fragment.

7. The method of claim 2 or claim 3, wherein the molecule binding the additional marker is an antibody or antibody fragment.

8. The method of claim 1, wherein the cell mixture has been obtained by stimulating T-cells in vivo.

9. The method of claim 1, wherein the cell mixture has been obtained by stimulating T-cells in vitro.

10. The method of claim 8 or claim 9, wherein the T-cells have been stimulated through their specific antigens or by polyclonal stimuli.

11. The method of claim 8 or claim 9, wherein the activated regulatory T-cells are separated during stimulation of cells in the cell mixture.

12. The method of claim 8 or claim 9, wherein the activated regulatory T-cells are separated after stimulation of cells in the cell mixture.

13. The method of claim 1, wherein the separation is performed by flow-cytometry or magnetic cell sorting.

14. The method of claim 1, wherein the molecule binding CD154 is coupled to a fluorescent dye, a hapten and/or a magnetic particle.

15. The method of claim 2 or claim 3, wherein the molecule binding the additional marker is coupled to a fluorescent dye, a hapten and/or a magnetic particle.

16. The method of claim 1, wherein the additional marker is CD25.

17. The method of claim 1, wherein the additional marker is CD137.

18. The method of claim 1, wherein the enriched cell population is enriched for cells that are specific for a particular antigen.

* * * * *

UNITED STATES PATENT AND TRADEMARK OFFICE
CERTIFICATE OF CORRECTION

PATENT NO. : 9,523,076 B2  
APPLICATION NO. : 12/878871  
DATED : December 20, 2016  
INVENTOR(S) : Anne Schönbrunn et al.

It is certified that error appears in the above-identified patent and that said Letters Patent is hereby corrected as shown below:

In the Claims

Claim 2, Line 5 (Column 22, Line 56): Delete "CLD154" and insert --CD154--.

Signed and Sealed this  
Ninth Day of January, 2018

Joseph Matal  
*Performing the Functions and Duties of the*  
*Under Secretary of Commerce for Intellectual Property and*  
*Director of the United States Patent and Trademark Office*